US011376391B2

(12) United States Patent
Doudkine et al.

(10) Patent No.: US 11,376,391 B2
(45) Date of Patent: Jul. 5, 2022

(54) RESPIRATORY PRESSURE THERAPY SYSTEM WITH NEBULISING HUMIDIFIER

(71) Applicant: RESMED PTY LTD, Bella Vista (AU)

(72) Inventors: Dimitri Anatolievich Doudkine, Sydney (AU); Andrew Chan, Sydney (AU); Tumul Gupta, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 427 days.

(21) Appl. No.: 16/328,013

(22) PCT Filed: Aug. 28, 2017

(86) PCT No.: PCT/AU2017/050912
§ 371 (c)(1),
(2) Date: Feb. 25, 2019

(87) PCT Pub. No.: WO2018/035579
PCT Pub. Date: Mar. 1, 2018

(65) Prior Publication Data
US 2019/0192809 A1    Jun. 27, 2019

(30) Foreign Application Priority Data
Aug. 26, 2016  (AU) ............................... 2016903417

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0066* (2013.01); *A61M 16/024* (2017.08);
(Continued)

(58) Field of Classification Search
CPC .............. A61M 16/00; A61M 16/0054; A61M 16/0057; A61M 16/0066; A61M 16/01;
(Continued)

(56) References Cited

U.S. PATENT DOCUMENTS 3,865,106 A * 2/1975 Palush ................ A61M 16/162
128/200.18
4,782,832 A 11/1988 Trimble et al.
(Continued)

FOREIGN PATENT DOCUMENTS

| WO | 98/004310 | 2/1998 |
|---|---|---|
| WO | 98/034665 | 8/1998 |

(Continued)

OTHER PUBLICATIONS

Aerogen Aeroneb Solo® System Instruction Manual (Year: 2014).*
(Continued)

*Primary Examiner* — Joseph D. Boecker
(74) *Attorney, Agent, or Firm* — Nixon & Vanderhye P.C.

(57) ABSTRACT

Apparatus for treating a respiratory disorder in a patient, the apparatus comprising: a respiratory pressure therapy device configured to generate a flow of air for treating the respiratory disorder, said flow of air being at a positive pressure with respect to ambient pressure; an air circuit adapted to transport said flow of air generated by said respiratory pressure therapy device to a patient interface, said air circuit having a proximal end connectable to said respiratory pressure therapy device and a distal end connectable to said patient interface; a nebuliser module located at or adjacent to said proximal end of said air circuit, said nebuliser module adapted to nebulise a liquid to form a nebula of said liquid, and to admit said nebula into said flow of air generated by said respiratory pressure therapy device; and a vaporiser located at said distal end of said air circuit, said (Continued)

vaporiser adapted to receive said nebula and further adapted to vaporise said nebula to form a humidified flow of air. Also, a method for treating a respiratory disorder in a patient, the method comprising the steps of: generating a flow of air for treating the respiratory disorder in a respiratory pressure therapy device, said flow of air being at a positive pressure with respect to ambient pressure; nebulising a liquid retained in a water reservoir to form a nebula of said liquid, and admitting said nebula to said flow of air; transporting said flow of air and said nebula over an air circuit; receiving said flow of air and said nebula in a vaporiser module; vaporising said nebula to form a vapour of said liquid; mixing said air flow with said vapour in said vaporiser module to form a humidified flow of air; receiving said humidified flow of air in a patient interface; and delivering said humidified flow of air to said patient for treatment of said respiratory disorder.

18 Claims, 23 Drawing Sheets

(51) Int. Cl.
*A61M 16/06* (2006.01)
*A61M 16/10* (2006.01)
*A61M 16/14* (2006.01)

(52) U.S. Cl.
CPC ........ *A61M 16/06* (2013.01); *A61M 16/0683* (2013.01); *A61M 16/107* (2014.02); *A61M 16/109* (2014.02); *A61M 16/1045* (2013.01); *A61M 16/142* (2014.02); *A61M 16/161* (2014.02); *A61M 16/162* (2013.01); *A61M 16/0051* (2013.01); *A61M 16/026* (2017.08); *A61M 16/1095* (2014.02); *A61M 16/145* (2014.02); *A61M 2016/0027* (2013.01); *A61M 2016/0039* (2013.01); *A61M 2202/0208* (2013.01); *A61M 2205/15* (2013.01); *A61M 2205/215* (2013.01); *A61M 2205/3334* (2013.01); *A61M 2205/3344* (2013.01); *A61M 2205/3365* (2013.01); *A61M 2205/3368* (2013.01); *A61M 2205/3653* (2013.01); *A61M 2205/42* (2013.01); *A61M 2206/14* (2013.01); *A61M 2230/42* (2013.01)

(58) Field of Classification Search
CPC ...... A61M 16/06; A61M 16/08; A61M 16/10; A61M 16/104; A61M 16/1045; A61M 16/1075; A61M 16/108; A61M 16/1085; A61M 16/109; A61M 16/1095; A61M 16/14; A61M 16/142; A61M 16/16; A61M 16/162; A61M 16/165
See application file for complete search history.

(56) References Cited

U.S. PATENT DOCUMENTS

| | | | | |
|---|---|---|---|---|
| 4,944,310 | A | 7/1990 | Sullivan | |
| 6,532,959 | B1 | 3/2003 | Berthon-Jones | |
| 6,581,594 | B1 | 6/2003 | Drew et al. | |
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 10,881,829 | B2 | 1/2021 | Goff et al. | |
| 2005/0217666 | A1* | 10/2005 | Fink | A61M 16/0858 128/200.14 |
| 2008/0078386 | A1* | 4/2008 | Feldhahn | A61M 16/16 128/204.18 |
| 2008/0223953 | A1* | 9/2008 | Tomono | F24F 6/12 239/102.2 |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2011/0146670 | A1* | 6/2011 | Gallem | A61M 16/0833 128/200.14 |
| 2012/0125333 | A1* | 5/2012 | Bedford | A61M 16/06 128/203.25 |
| 2012/0125334 | A1* | 5/2012 | Korneff | A61M 16/109 128/203.26 |
| 2013/0255670 | A1* | 10/2013 | Ott | A61M 16/16 128/200.14 |
| 2014/0109899 | A1* | 4/2014 | Boucher | A61M 16/14 128/200.18 |
| 2014/0202462 | A1* | 7/2014 | Stoks | A61M 16/0883 128/204.18 |
| 2014/0224247 | A1* | 8/2014 | Tan | A61M 16/14 128/203.14 |
| 2015/0352299 | A1* | 12/2015 | Cortez, Jr. | A61M 11/06 128/200.23 |
| 2016/0250438 | A1* | 9/2016 | Harwood | A61M 16/0875 128/201.13 |
| 2016/0279351 | A1* | 9/2016 | Gallem | A61M 15/0028 |
| 2017/0216552 | A1* | 8/2017 | Goff | A61M 16/1095 |
| 2017/0312472 | A1* | 11/2017 | Kirton | A61M 16/14 |
| 2018/0078728 | A1* | 3/2018 | Holyoake | A61M 16/0875 |
| 2018/0296776 | A1* | 10/2018 | Yener | A24F 1/30 |

FOREIGN PATENT DOCUMENTS

| | | |
|---|---|---|
| WO | 00/078381 | 12/2000 |
| WO | 2004/073778 | 9/2004 |
| WO | 2005/063328 | 7/2005 |
| WO | 2006/074513 | 7/2006 |
| WO | 2006/130903 | 12/2006 |
| WO | 2009/052560 | 4/2009 |
| WO | 2010/135785 | 12/2010 |
| WO | 2012/045051 | 4/2012 |
| WO | 2012/080923 | 6/2012 |
| WO | 2012/171072 | 12/2012 |
| WO | 2013/020167 | 2/2013 |

OTHER PUBLICATIONS

International Search Report for PCT/AU2017/050912 dated Dec. 14, 2017, 6 pages.
"*Respiratory Physiology*", by John B. West, Lippincott Williams & Wilkins, 9th edition published 2012 (8 pages).

* cited by examiner

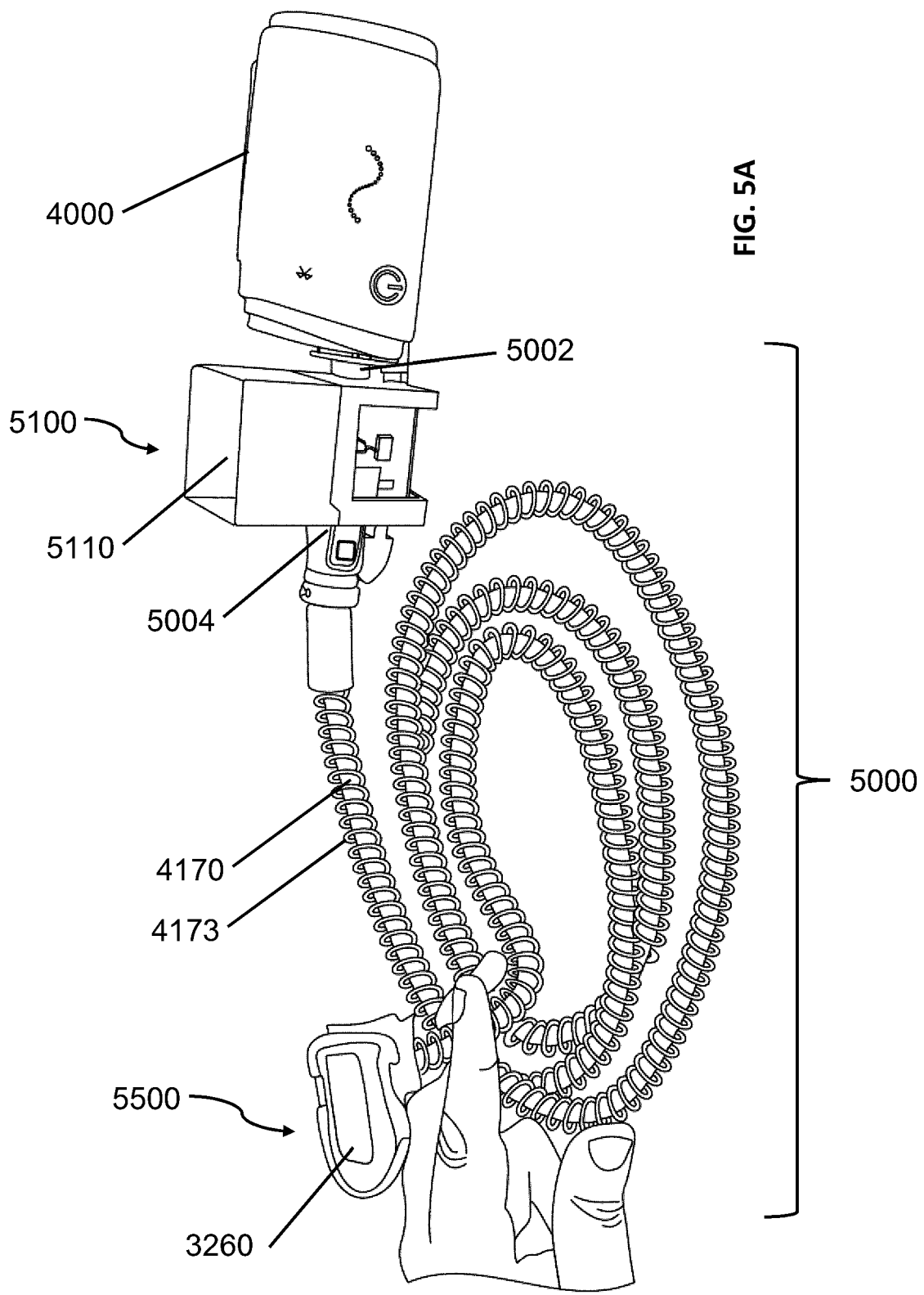

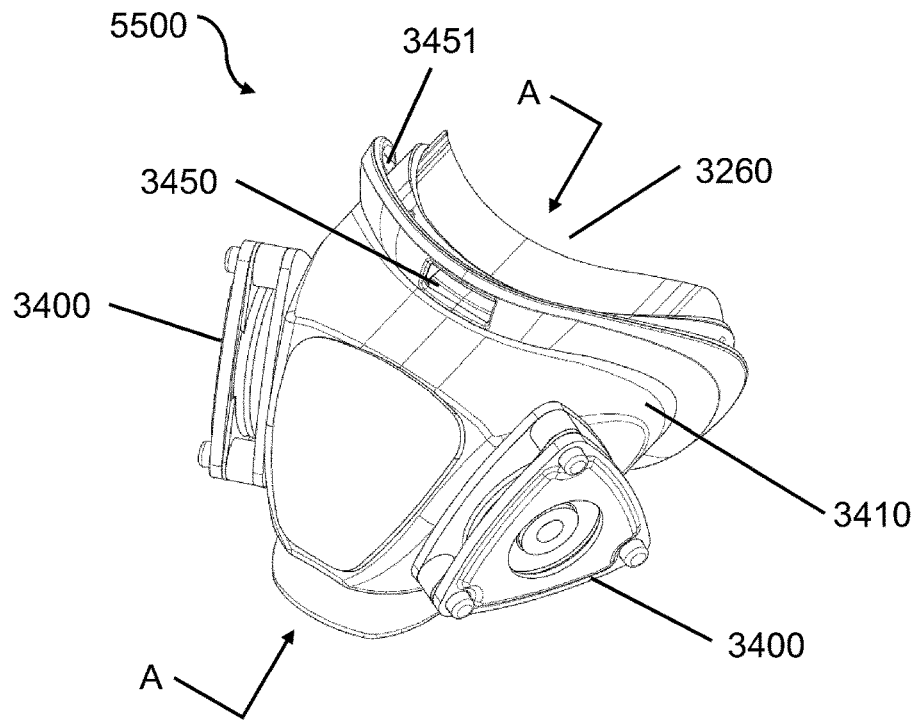
FIG. 8B
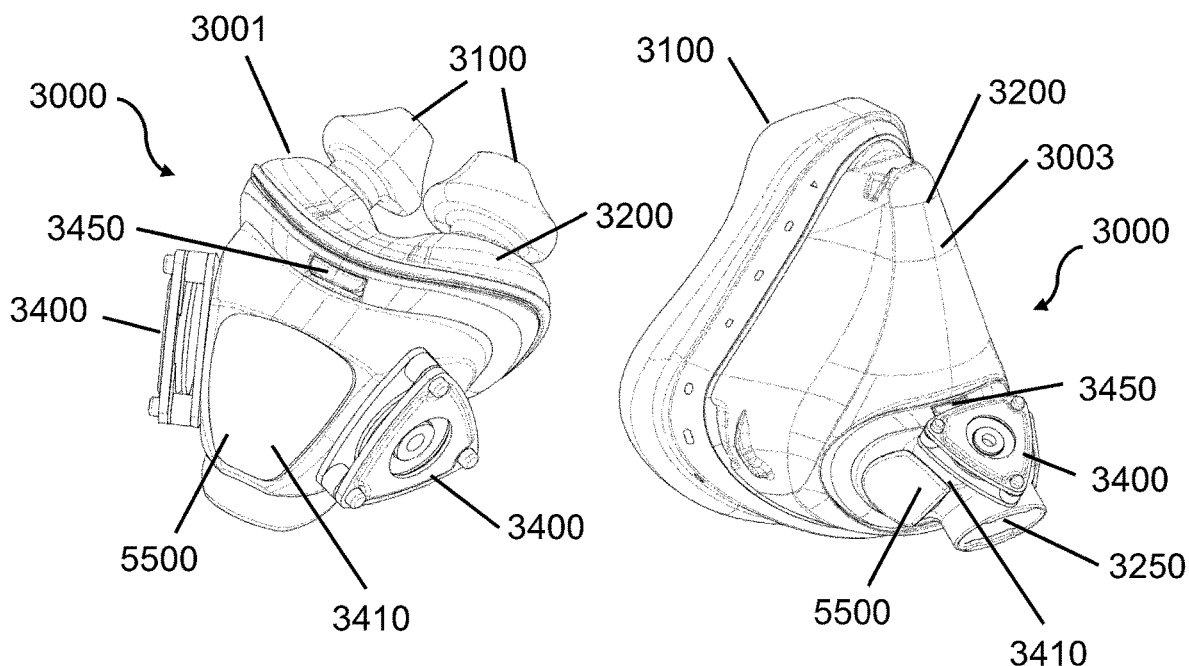
FIG. 8C     FIG. 8D

RESPIRATORY PRESSURE THERAPY SYSTEM WITH NEBULISING HUMIDIFIER

This application is the U.S. national phase of International Application No. PCT/AU2017/050912 filed Aug. 28, 2017 which designated the U.S. and claims priority to AU Patent Application No. 2016903417 filed Aug. 26, 2016, the entire contents of each of which are hereby incorporated by reference.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use.

1.2 Description of the Related Art 1.2.1 Human Respiratory System and its Disorders The respiratory system of the body facilitates gas exchange. The nose and mouth form the entrance to the airways of a patient.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Various therapies, such as Continuous Positive Airway Pressure (CPAP) therapy, Non-Invasive Ventilation (NIV) and Invasive Ventilation (IV) have been used to treat one or more of the above respiratory disorders.

1.2.3 Treatment Systems

These therapies may be provided by a treatment system or device. A treatment system may comprise a Respiratory Pressure Therapy device (RPT device), an air circuit, a humidifier, a patient interface, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

1.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

1.2.3.3 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a humidifier for medical use, e.g. a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

In certain prior art medical humidifiers, condensation in the air circuit can be a problem for patients. If water condenses in the air circuit while a patient is wearing the system, some water may enter the patient's airways. In some cases, water may flow back towards a respiratory therapy device, and/or the humidifier, which may potentially then create a risk of damaging or interfering with an operation of the device and/or the humidifier. For example, water may interfere with internal electronics, occlude a flow path, occlude a sensing port, leak and create a hazard, and/or create 'gurgling' noise as it is splashed about by the flow of air.

To mitigate this risk, the air circuit may be heated in some instances of the prior art. However, this may increase a cost and complexity of the air circuit, as well as decreasing an overall efficiency of the RPT system, as heat from the air circuit is lost to the ambient due to the temperature difference between the heated air circuit and the ambient. This may lead to an increase in cost/bulk of the therapy system, including from an increased power requirements to power the heated air circuit.

Furthermore, some prior art humidifiers may suffer from a slow response time, for example at start-up, or during operation.

It is an object of the invention to address one or more of the foregoing problems or at least provide the public with a useful choice.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of the present technology is a medical humidification system.

An aspect of certain forms of the present technology is to provide a respiratory pressure treatment system comprising a medical humidification system which provides increased comfort to a patient. An aspect of certain forms of the present technology is to provide methods and/or apparatus that improve the compliance of patients with respiratory therapy.

One form of the present technology provides an energy efficient humidification system for medical use.

One aspect of the present technology is a humidification system for medical use which is less likely to give rise to condensation in an air circuit.

One aspect of the present technology is a humidification system for medical use for a patient which provides a supply of air with water droplets to travel along an air circuit, and which vaporises the water droplets at an end of the air circuit close to the patient.

One aspect of the present technology is a humidification system for medical use comprising a nebuliser, an air circuit and a vaporiser.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

According to one aspect of the present technology, there is provided an apparatus or system for treating a respiratory disorder in a patient. The apparatus may comprise a respiratory pressure therapy device. The respiratory pressure therapy device may be configured to generate a flow of air for treating the respiratory disorder. The flow of air may be at a positive pressure with respect to ambient pressure.

The apparatus may further comprise an air circuit adapted to transport the flow of air generated by the respiratory pressure therapy device to a patient interface. The air circuit may have a proximal end connectable to the respiratory pressure therapy device and a distal end connectable to the patient interface.

The apparatus may further comprise a nebuliser module located at or adjacent to the proximal end of the air circuit. The nebuliser module may be adapted to nebulise a liquid to form a nebula of the liquid. The nebuliser may be further adapted to admit the nebula into the flow of air generated by the respiratory pressure therapy device.

The apparatus may further comprise a vaporiser located at the distal end of the air circuit. The vaporiser may be adapted to receive the nebula. The vaporiser may be further adapted to vaporise the nebula to form a humidified flow of air.

The apparatus may further comprise a patient interface adapted for receiving the humidified flow of air and providing the humidified flow of air to the patient for treating the respiratory disorder.

The apparatus may further comprise a reservoir adapted to retain the liquid.

One form of the present technology provides a treatment system for treating a respiratory disorder in a patient. The system may comprise a respiratory pressure therapy device configured to generate a flow of air at a positive pressure with respect to ambient pressure, an air circuit adapted to transport the flow of air to a patient interface, a water reservoir configured to retain a volume of water for humidification of the flow of air, a nebuliser module adapted to receive water from the water reservoir and to generate a nebula, and to admit the nebula into the flow of air for delivery to a vaporiser module, and the vaporiser module adapted to receive the nebula and comprising a heating element configured to generate heat to vaporise the received nebula to humidify the flow of air.

The vaporiser module may be directly connectable to the patient interface.

The heating element may be formed of a thermally conductive material comprising one or more of a metal, a polymer, or a ceramic.

The vaporiser module may comprise a labyrinthine path therethrough for the nebula and the flow of air.

The nebuliser module may be configured to admit the nebula into the flow of air parallel to the flow of air.

The nebuliser module may comprise the water reservoir.

The nebuliser module may comprise a nebuliser configured to float in the water reservoir.

The nebuliser module may be located proximal to the respiratory pressure therapy device.

The air circuit may be located between the nebuliser module and the vaporiser module.

The treatment system may further comprise a liquid filter located downstream of the vaporiser module and configured to block passage of liquid water therethrough.

The air circuit may comprise a wire circuit to provide power and signalling to the vaporiser module.

The air circuit may further comprise a hydrophobic coating on an inner surface thereof.

Another form of the present technology provides a nebuliser apparatus for a respiratory treatment system, the respiratory treatment system for treating a respiratory disorder in a patient. The nebuliser apparatus may comprise an air inlet for receiving a flow of air at a positive pressure with respect to ambient pressure, a nebuliser configured to receive a supply of water, generate a nebula from the supply of water, and admit the nebula into the flow of air. The nebuliser apparatus may further comprise an outlet for the flow of air comprising the nebula, wherein the nebuliser module is configured to admit the nebula into the flow of air parallel to the flow of air.

The nebuliser apparatus may further comprise a water reservoir configured to retain a volume of water, the nebuliser being configured to receive the supply of water from the water reservoir.

The nebuliser may be configured to float in the water reservoir.

Another form of the present technology provides a vaporiser apparatus for a respiratory treatment system, the respiratory treatment system for treating a respiratory disorder in a patient. The vaporiser apparatus may comprise a vaporiser inlet for receiving a nebula in a flow of air at a positive pressure with respect to ambient pressure, a heating element configured to generate heat to vaporise the received nebula to humify the flow of air, and a vaporiser outlet for the humidified flow of air. The vaporiser inlet and the vaporiser outlet may each be configured to be directly connectable to respective parts of an air circuit.

Another form of the present technology provides a vaporiser apparatus for a respiratory treatment system, the respiratory treatment system for treating a respiratory disorder in a patient. The vaporiser apparatus may comprise a vaporiser inlet for receiving a nebula in a flow of air at a positive pressure with respect to ambient pressure, a heating element configured to generate heat to vaporise the received nebula to humidify the flow of air, and a vaporiser outlet for the humidified flow of air. The vaporiser apparatus may be configured to be directly connectable to a patient interface.

The heating element may be formed of a thermally conductive material comprising one or more of a metal, a polymer, or a ceramic.

The vaporiser apparatus may comprise a labyrinthine path therethrough for the nebula and the flow of air.

The vaporiser apparatus may comprise one or more sensors adapted for sensing one or more parameters of the flow of air in the vaporiser outlet, wherein the one or more parameters comprise one or more of: temperature; flow rate; pressure; and humidity of the flow of air in the vaporiser outlet.

The vaporiser apparatus may comprise a vent for venting a flow of exhaled gases from a patient.

The vent may be positioned such that any water vapour in the flow of exhaled gas from the patient is available for vaporising by the heating element for humidifying the flow of air before venting through the vent.

The vaporiser apparatus may comprise a vaporiser housing structured to mate, in use, with a supporting structure of the patient interface.

The vaporiser housing may comprise one or more connecting surfaces surrounding the vaporiser outlet, the one or more connecting surfaces being structured to mate, in use, with a supporting structure of the patient interface.

Another form of the present technology provides a respiratory apparatus for use in treating a respiratory disorder in a patient. The system may comprise a vaporiser apparatus comprising a vaporiser inlet for receiving a nebula in a flow of air at a positive pressure with respect to ambient pressure, a heating element configured to generate heat to vaporise the received nebula to humidify the flow of air, and a vaporiser outlet for the humidified flow of air, and a patient interface directly connected to the vaporiser apparatus.

The vaporiser apparatus may comprise a vaporiser housing and the patient interface comprises a plenum chamber, wherein the vaporiser housing is connected to the plenum chamber.

The vaporiser housing may comprise one or more connecting surfaces surrounding the vaporiser outlet, the one or more connecting surfaces being connected to a supporting structure of the plenum chamber.

The respiratory apparatus may comprise a vent for venting a flow of exhaled gases from a patient.

The vent may be provided in the vaporiser housing.

An aspect of one form of the present technology is a method of manufacturing apparatus in any of the previous aspects.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a respiratory pressure treatment (RPT) system including a patient 1000 wearing a patient interface 3000, in the form of nasal pillows, receiving a supply of air at positive pressure from a RPT device 4000. Air from the RPT device 4000 is humidified in a humidifier 5000*a*, and passes along an air circuit 4170 to the patient 1000. A bed partner 1100 is also shown. The patient 1000 is sleeping in a supine sleeping position.

FIG. 1B shows a system including a patient 1000 wearing a patient interface 3000, in the form of a nasal mask, receiving a supply of air at positive pressure from a RPT device 4000. Air from the RPT device is humidified in a humidifier 5000*a*, and passes along an air circuit 4170 to the patient 1000.

FIG. 1C shows a system including a patient 1000 wearing a patient interface 3000, in the form of a full-face mask, receiving a supply of air at positive pressure from a RPT device 4000. Air from the RPT device is humidified in a humidifier 5000*a*, and passes along an air circuit 4170 to the patient 1000. The patient 1000 is sleeping in a side sleeping position.

3.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

3.3 Patient Interface

FIG. 3 shows a patient interface in the form of a nasal mask in accordance with one form of the present technology.

3.4 RPT Device

3.5 Humidifier

FIG. 5A shows an isometric view of a RPT system in accordance with one form of the present technology.

Figure 5B:
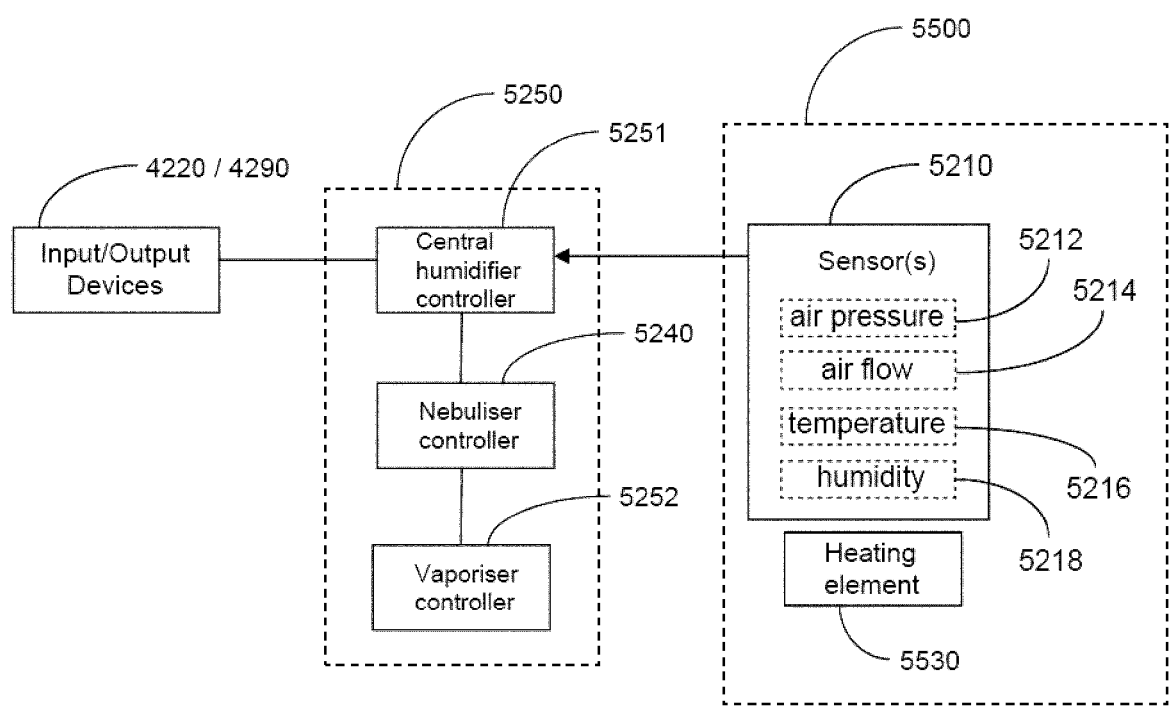

FIG. 5B shows a schematic of the electrical components of part of a RPT system in accordance with one form of the present technology.

Figure 6:
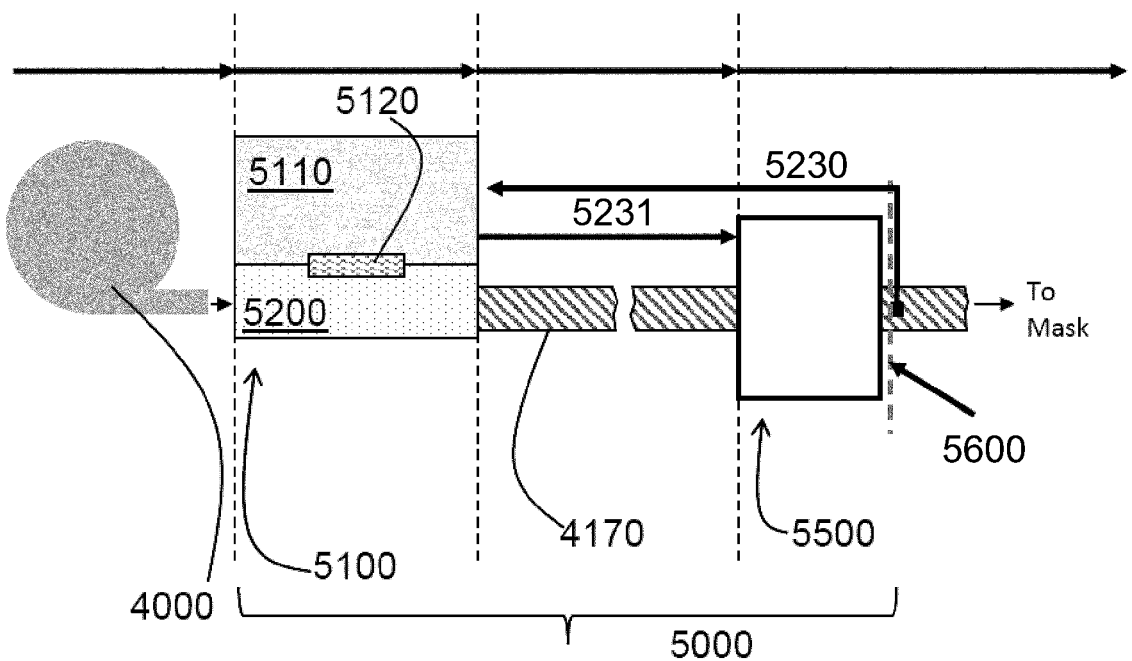
Figure 7A:
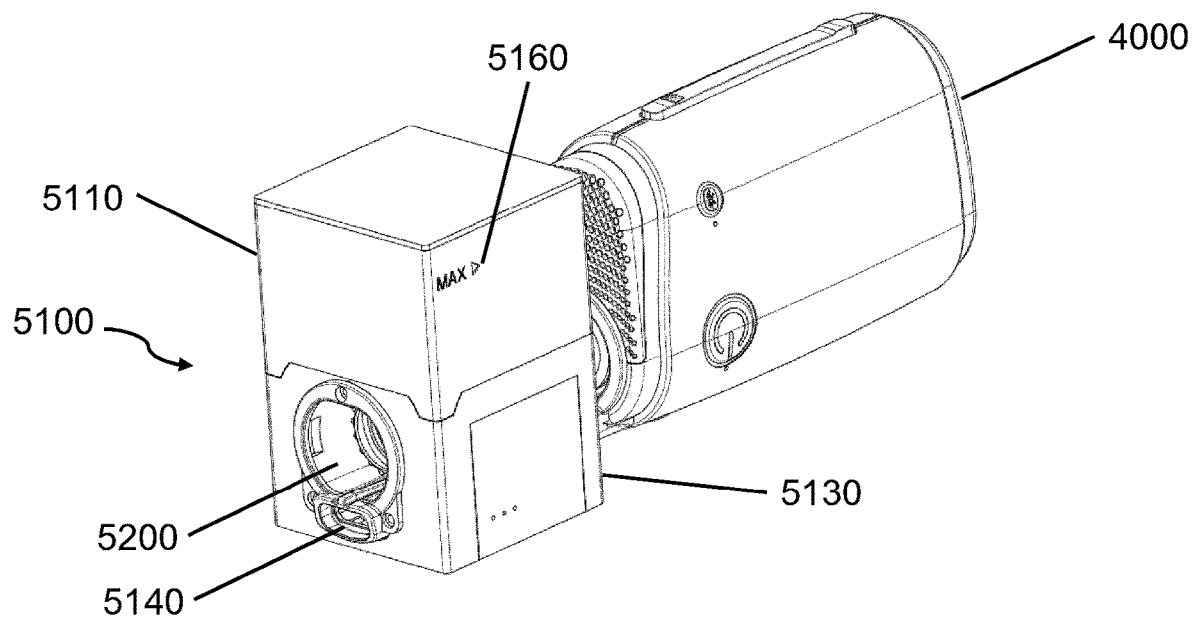
Figure 7B:
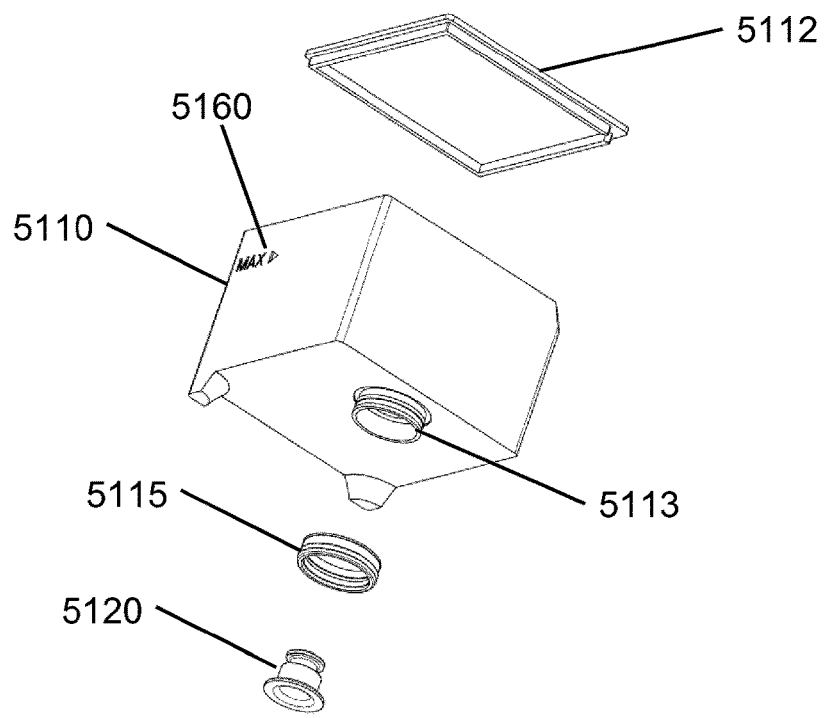
Figure 7C:
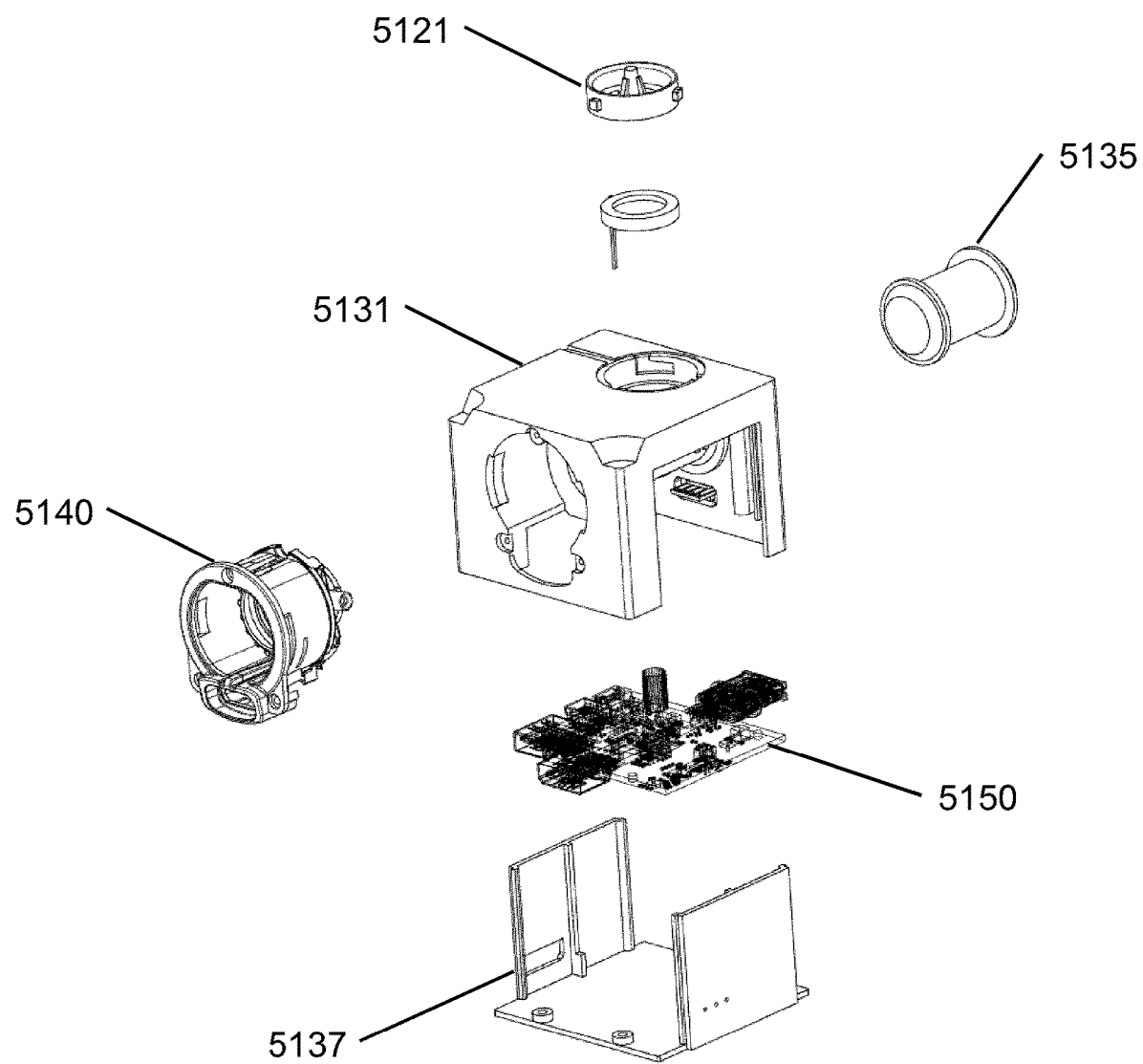
Figure 7D:
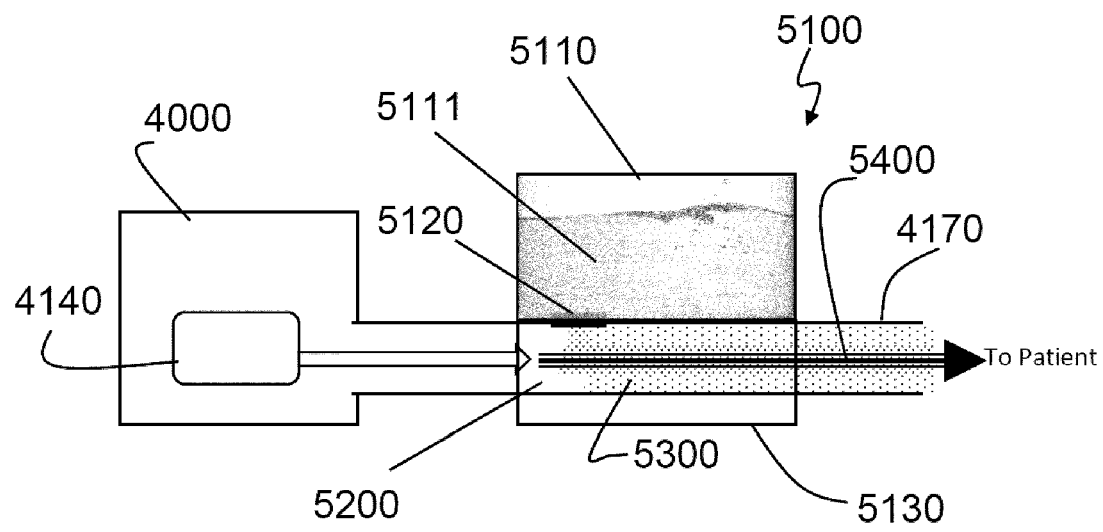
Figure 7E:
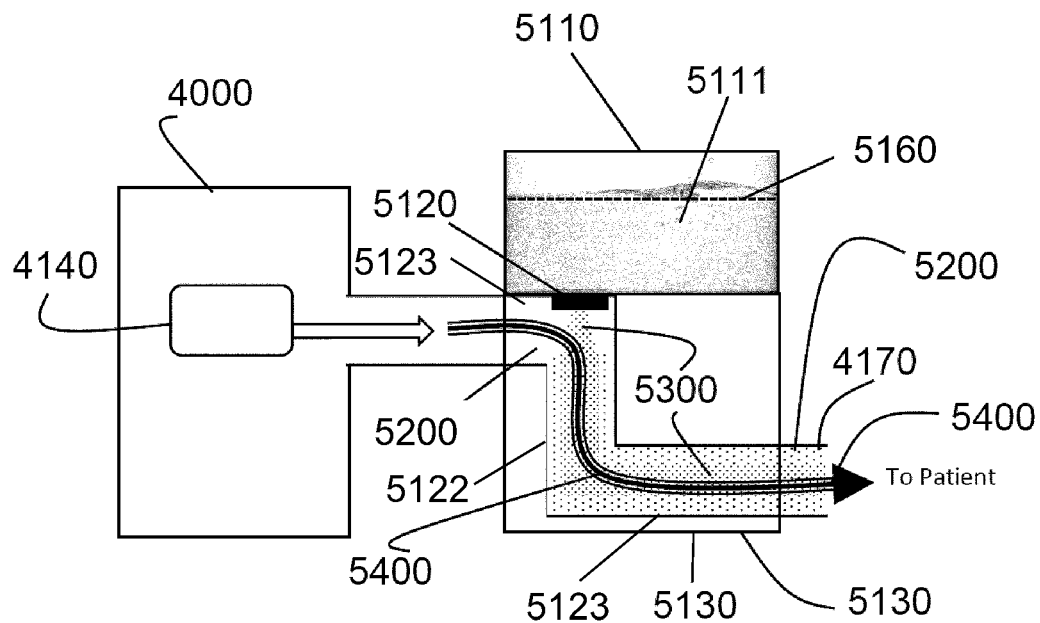
Figure 7F:
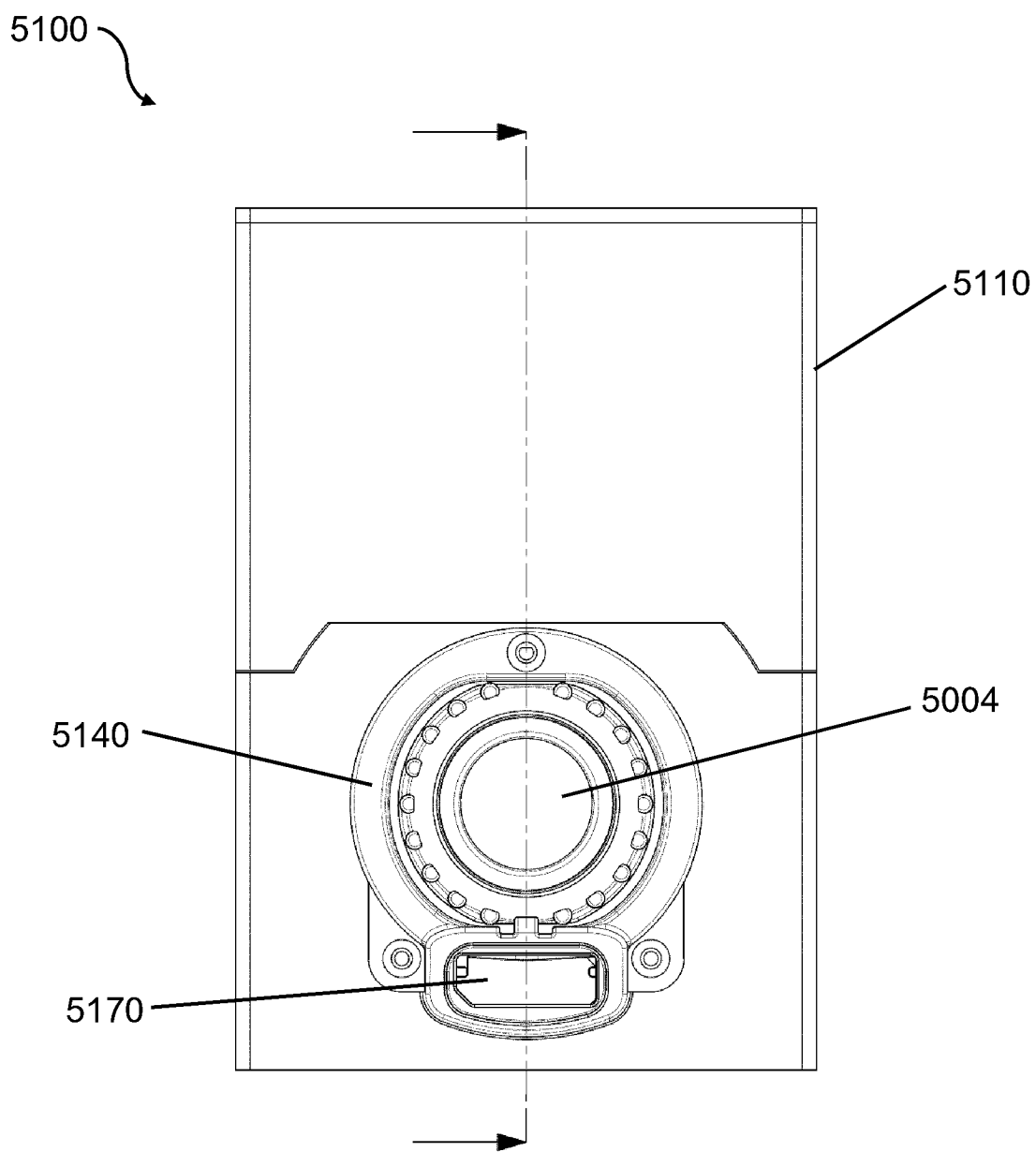
Figure 7G:
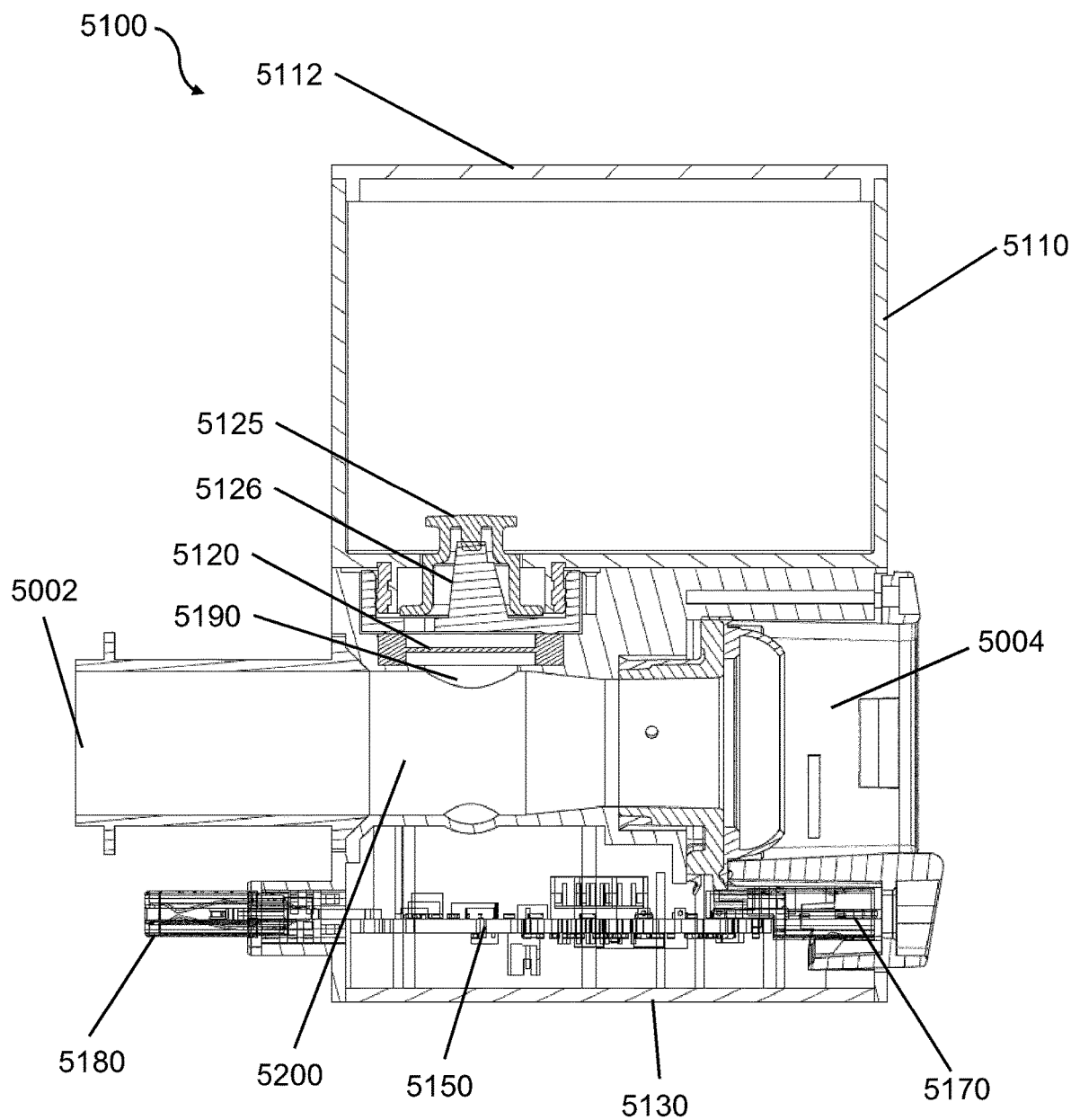
Figure 8A:
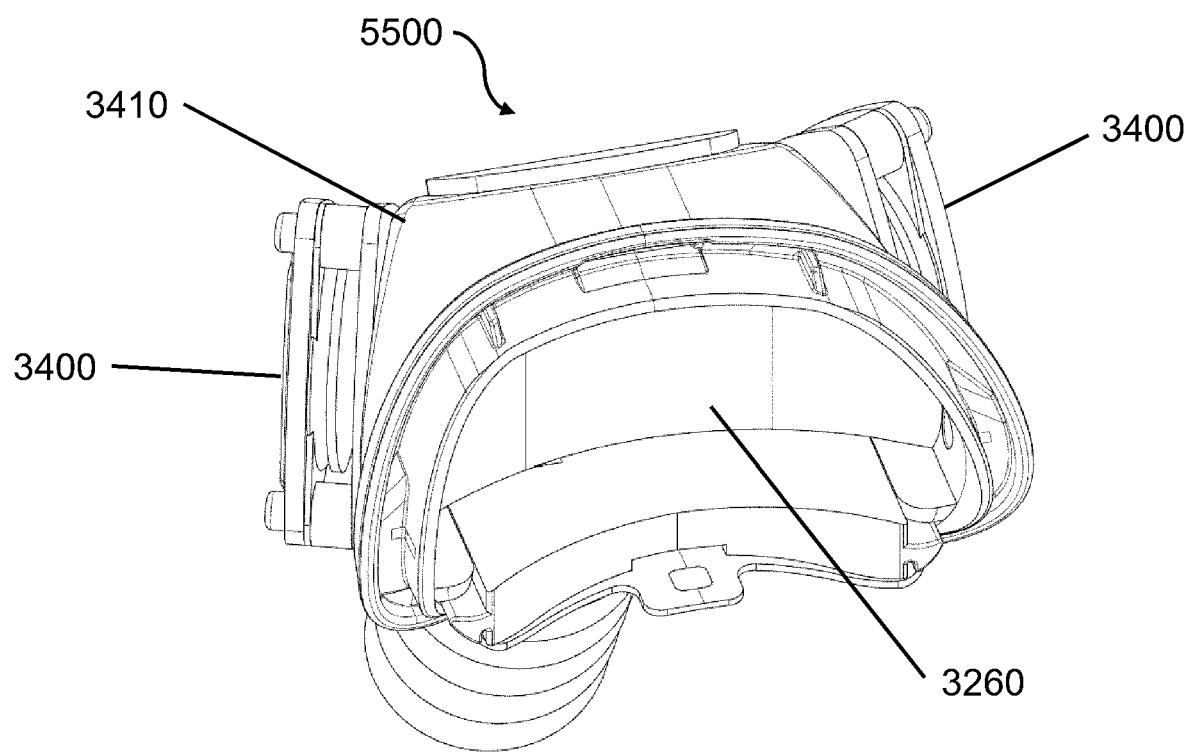
Figure 8E:
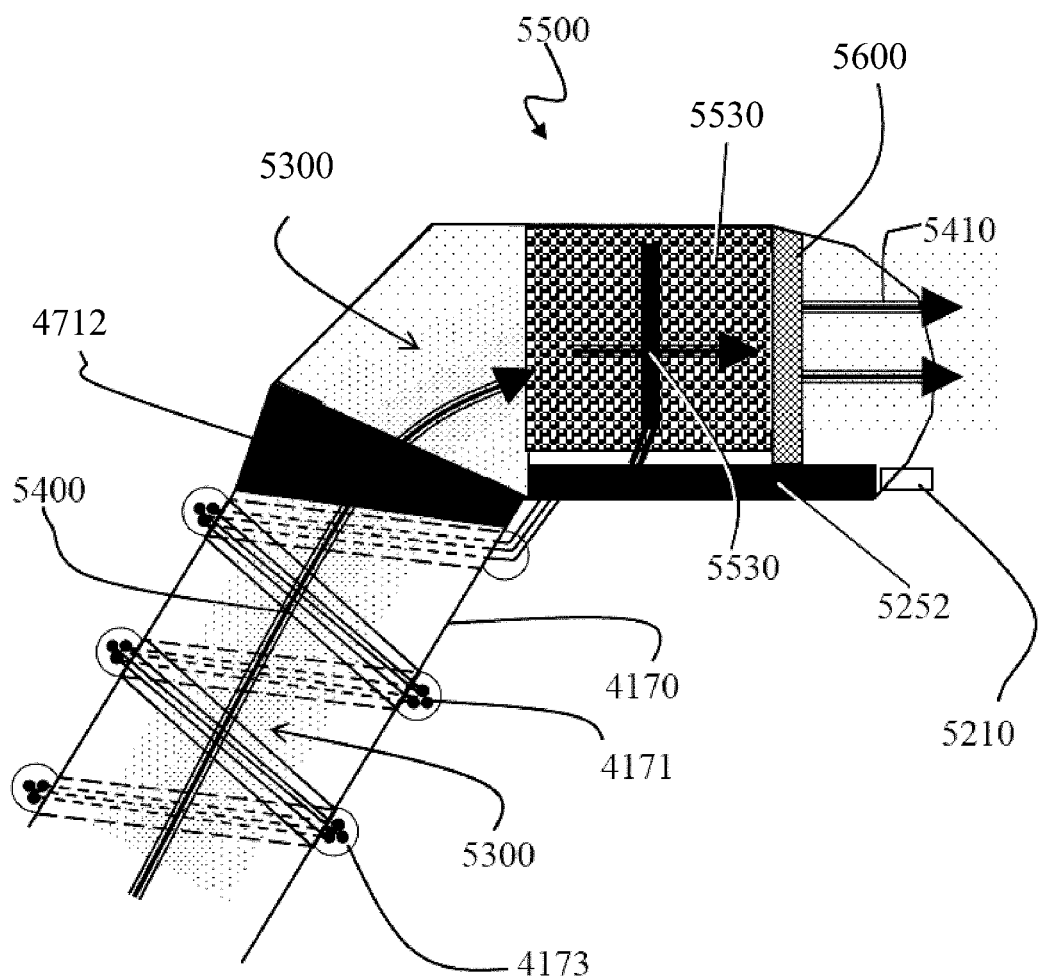
Figure 8F:
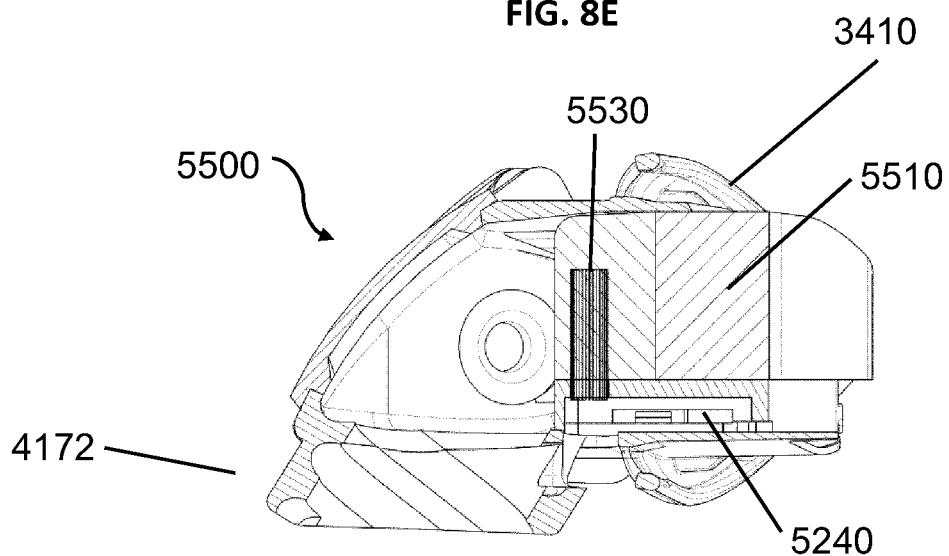
Figure 9A:
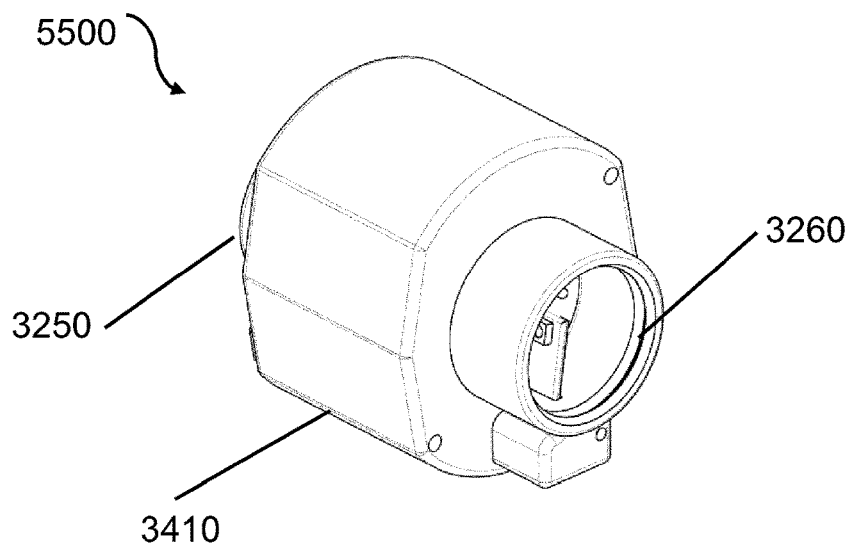
Figure 9B:
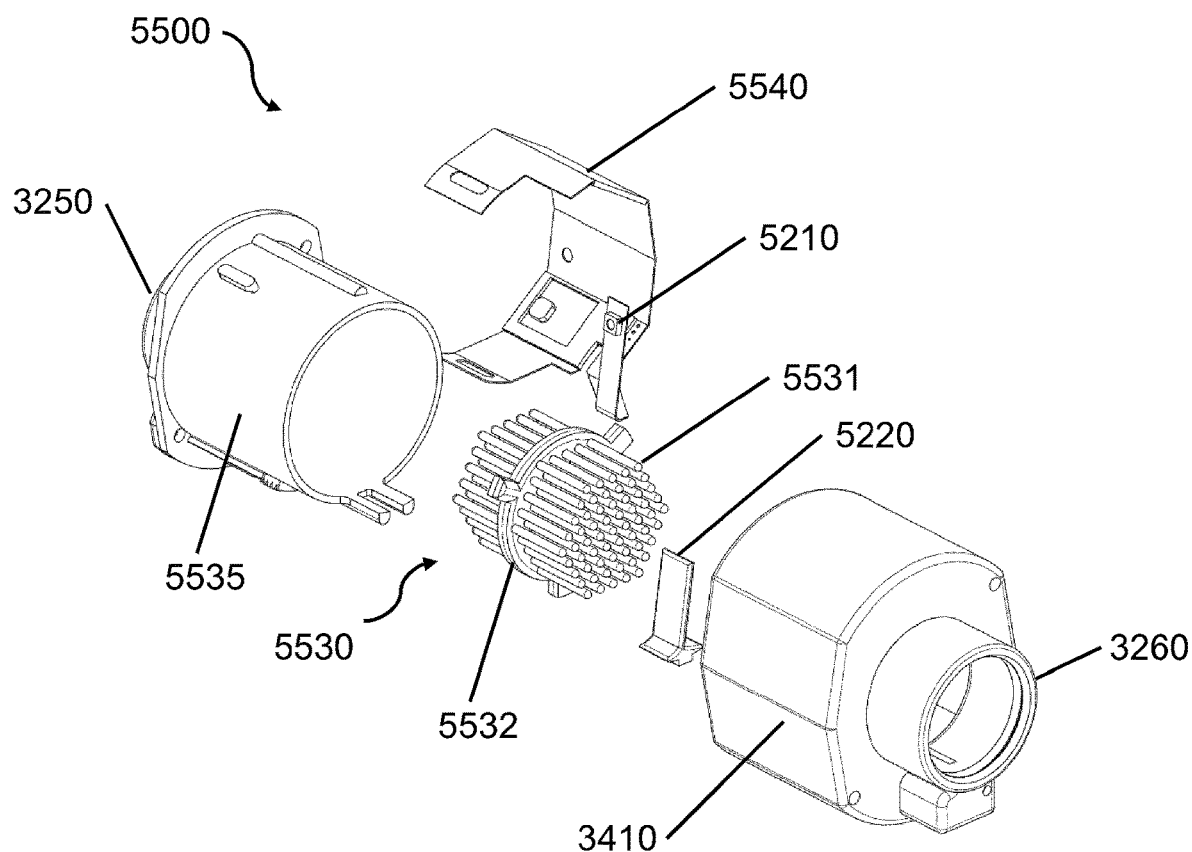

FIG. 6 shows a schematic view of a RPT system comprising a nebulising humidifier according to one form of the present technology;

FIG. 7A shows a part of a RPT system connected to a nebuliser module 5100 according to one form of the present technology;

FIG. 7B shows an exploded view of the water reservoir 5110 of the nebuliser module 5100 according to one form of the present technology;

FIG. 7C shows an exploded view of a nebuliser module housing according to one form of the present technology;

FIGS. 7D and 7E respectively show example arrangements of a nebuliser module 5100 according to one form of the present technology;

FIG. 7F shows an example of a nebuliser module 5100 according to certain forms of the present technology;

FIG. 7G shows a cross-sectional view of a nebuliser module 5100 along the dashed line of FIG. 7F;

FIGS. 8A and 8B are illustrations of a vaporiser module 5500 according to certain forms of the present technology;

FIGS. 8C and 8D show examples of an exemplary vaporiser module 5500 as disclosed herein attached to a patient interface, respectively a pillows-type patient interface 3001 and a full-face-type patient interface 3003 according to certain forms of the present technology;

FIG. 8E shows a schematic cross-sectional view of vaporiser module 5500 along line A-A of FIG. 8B;

FIG. 8F shows a schematic cross-sectional view of an alternate arrangement of a vaporiser module 5500 according to one form of the present technology;

FIGS. 9A and 9B shows example arrangements of an in-line vaporiser module 5500 according to certain forms of the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 Patient Interface

Figure 1A:
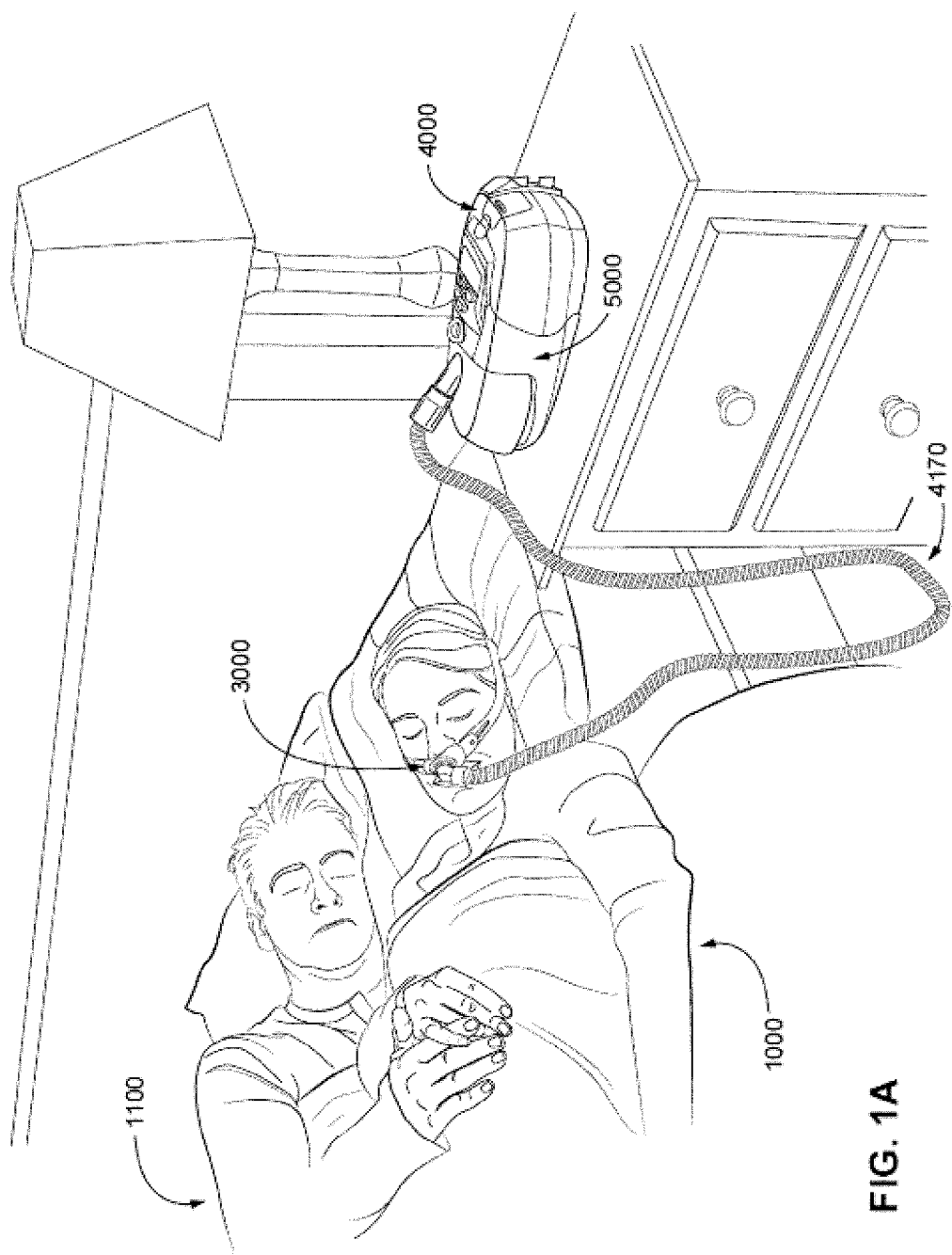
Figure 1B:
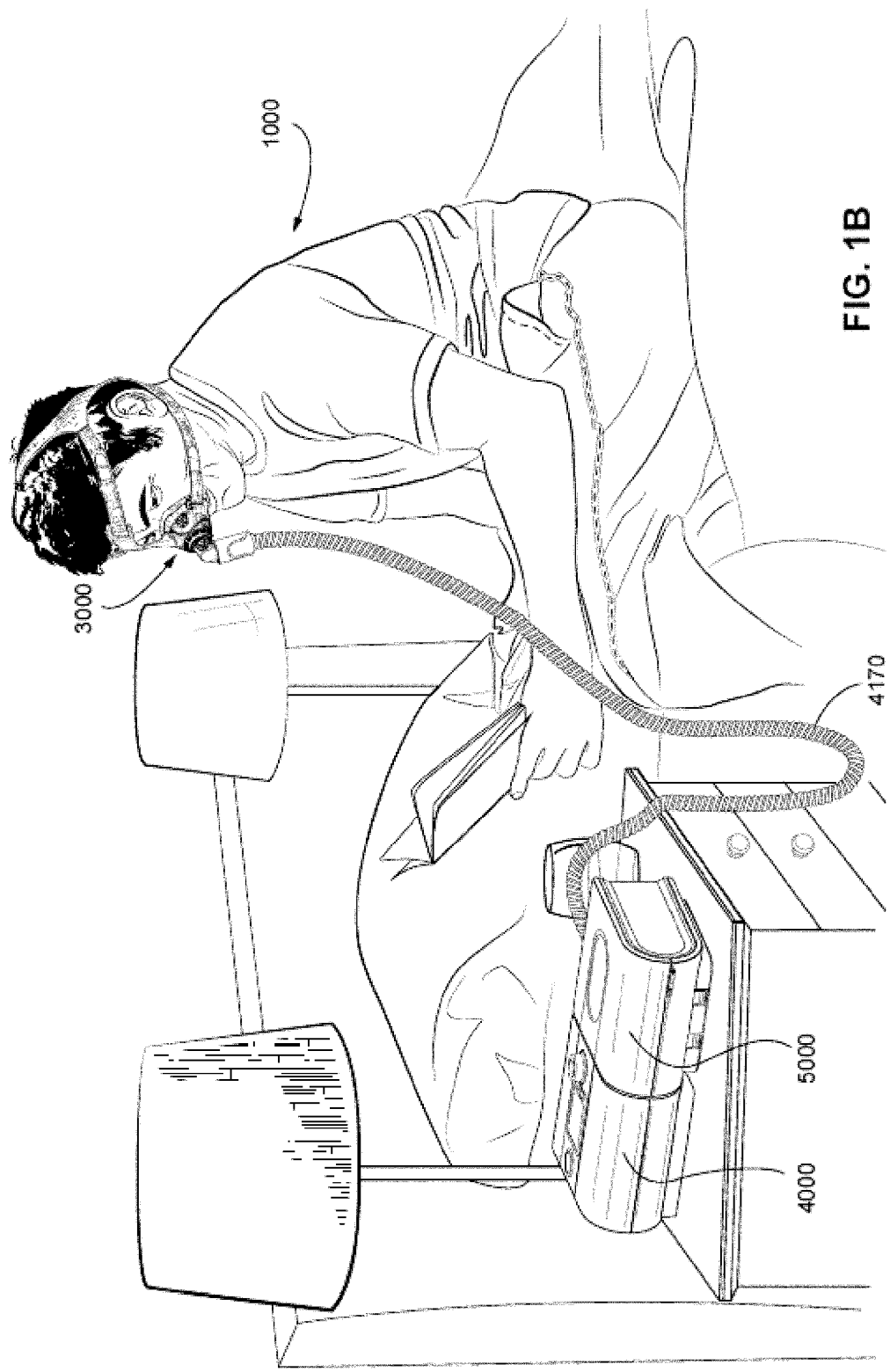
Figure 1C:
Figure 2:
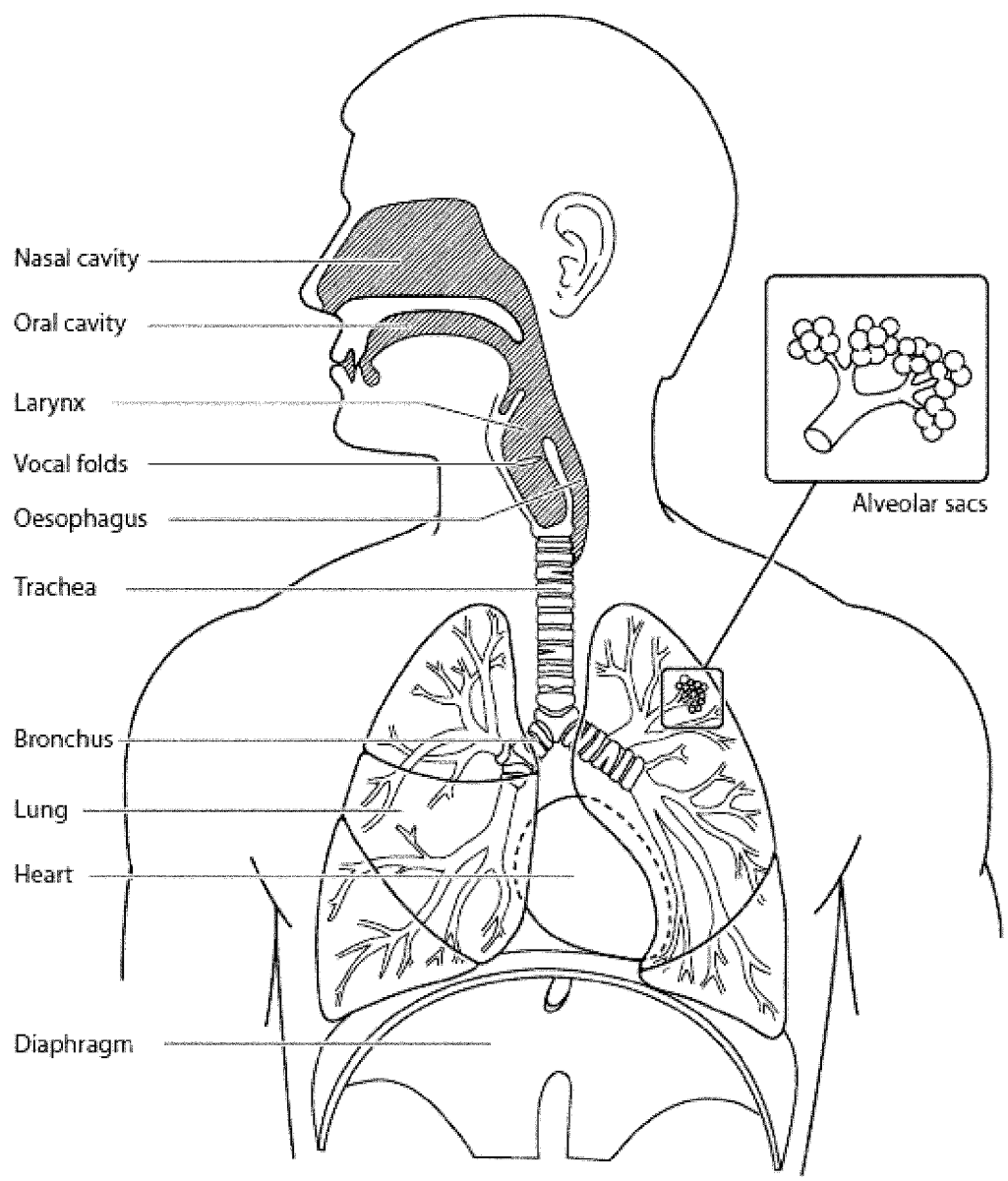
Figure 3:
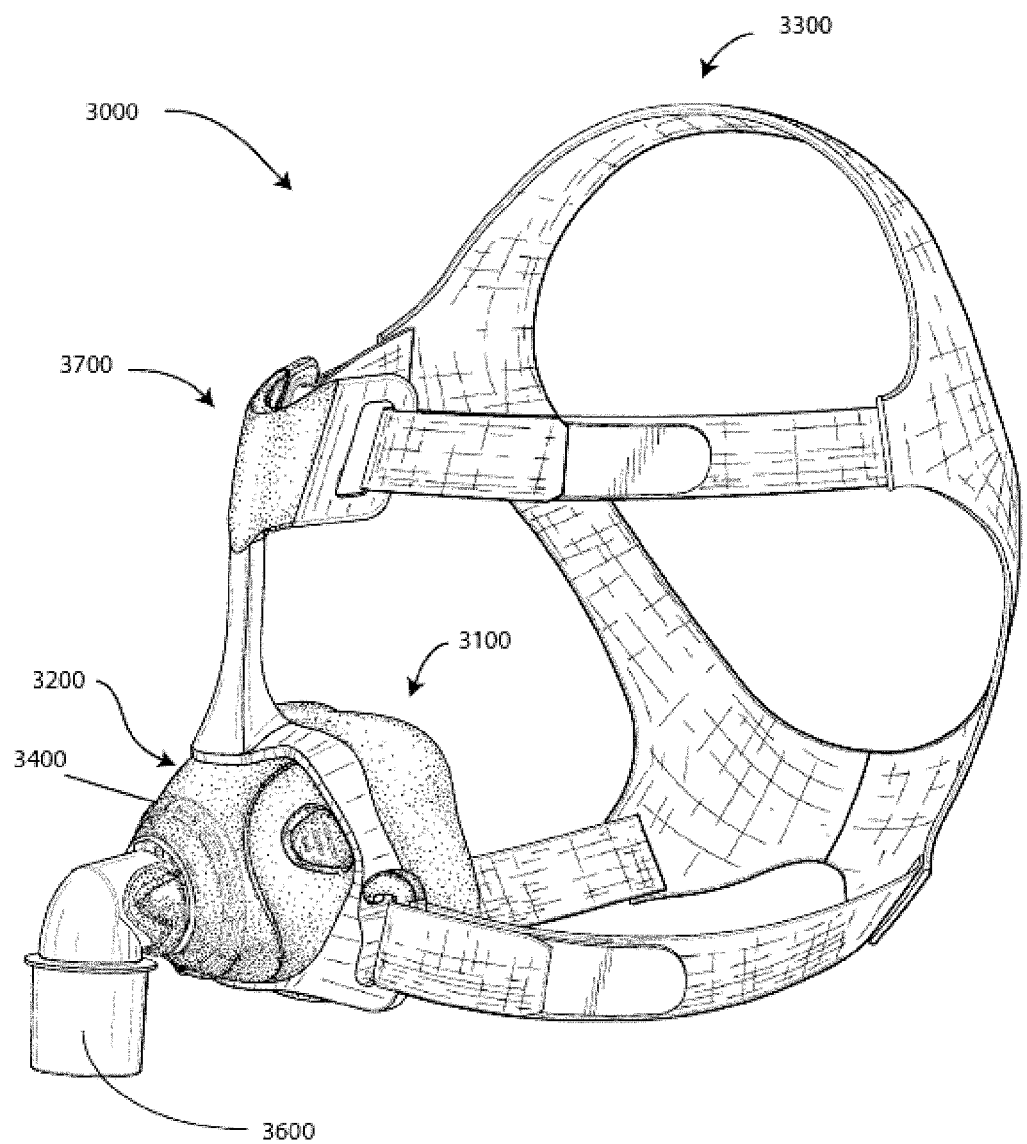

A non-invasive patient interface 3000 in accordance with one aspect of the present technology is shown in FIG. 3 and comprises the following functional aspects: a seal-forming structure 3100, a plenum chamber 3200, a positioning and stabilising structure 3300 (headgear), a vent 3400, one form of connection port 3600 for connection to air circuit 4170, and a forehead support 3700. In some forms a functional aspect may be provided by one or more physical components. In some forms, one physical component may provide one or more functional aspects. In use, the seal-forming structure 3100 is arranged to surround an entrance to the airways of the patient so as to facilitate the supply of air at positive pressure to the airways. The patient interface 3000 may comprise an anti-asphyxia valve.

If a patient interface is unable to comfortably deliver a minimum level of positive pressure to the airways, the patient interface may be unsuitable for respiratory pressure therapy.

The patient interface 3000 in accordance with some forms of the present technology is constructed and arranged to be able to provide a supply of air at a positive pressure of at least 6 $cmH_2O$, at least 10 $cmH_2O$ or at least 20 $cmH_2O$ with respect to ambient.

4.3.1 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

4.3.2 Vent

In one form, respiratory therapy system includes a vent 3400 constructed and arranged to allow for the washout of exhaled gases, e.g. carbon dioxide. In some forms, the patient interface 3000 may comprise the vent 3400. In other forms, the vent 3400 may be located elsewhere in the respiratory therapy system in addition to, or instead of, the patient interface 3000. For example, the respiratory therapy system may include a vent module located between the patient interface 3000 and the RPT device 4000, the vent module comprising a vent 3400.

In certain forms the vent 3400 is configured to allow a continuous vent flow from an interior of the plenum chamber 3200 to ambient whilst the pressure within the plenum chamber 3200 is positive with respect to ambient. The vent 3400 is configured such that the vent flow rate has a magnitude sufficient to reduce rebreathing of exhaled CO2 by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

4.3.3 Connection Port

Connection port 3600 of the patient interface 3000 allows for connection to the air circuit 4170.

4.4 RPT Device

An RPT device 4000 in accordance with one aspect of the present technology comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$ for respiratory therapy.

Figure 4A:
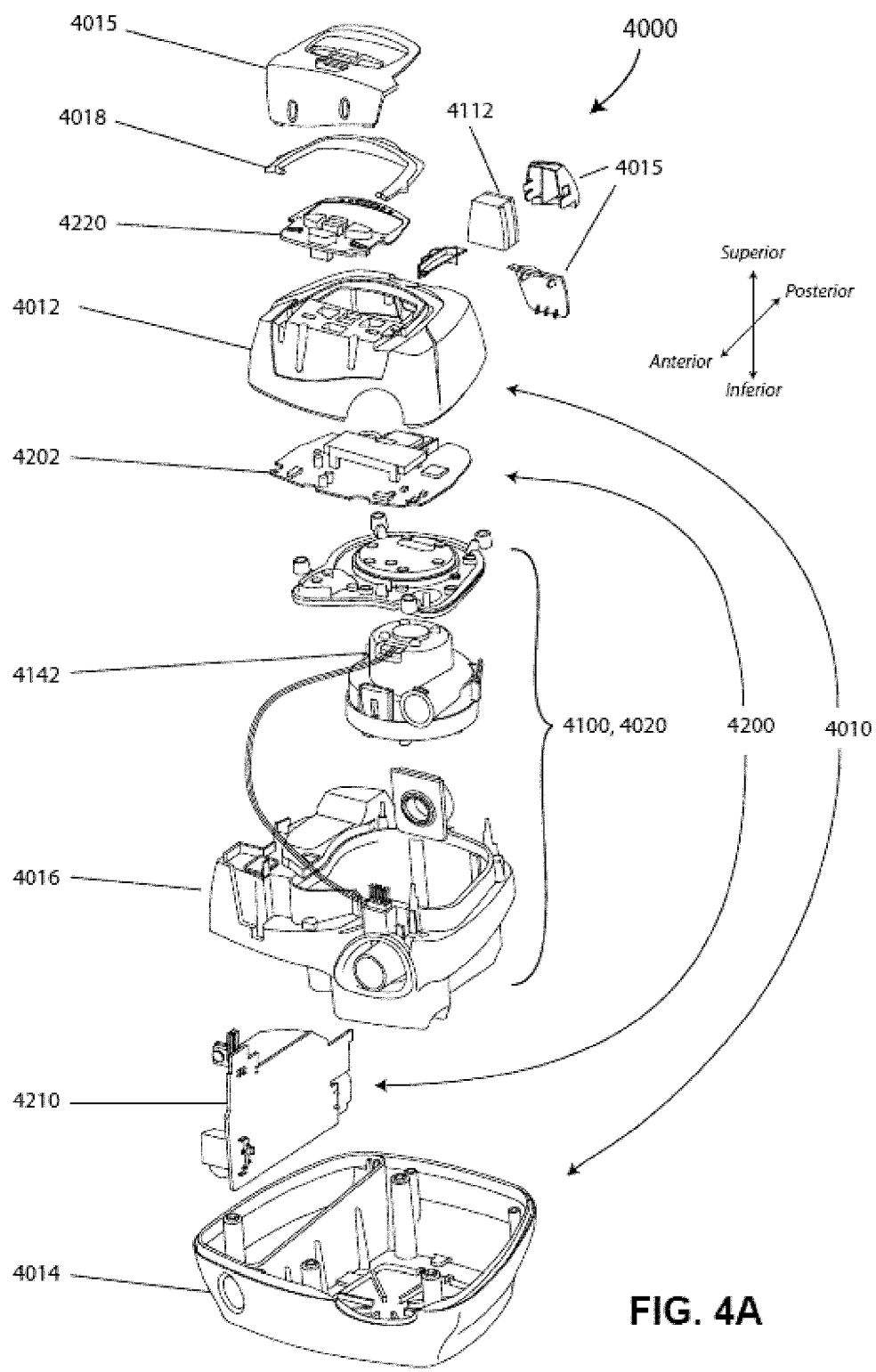
FIG. 4A shows a RPT device in accordance with one form of the present technology.

As seen in FIG. 4A, the RPT device 4000 may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

Figure 4B:
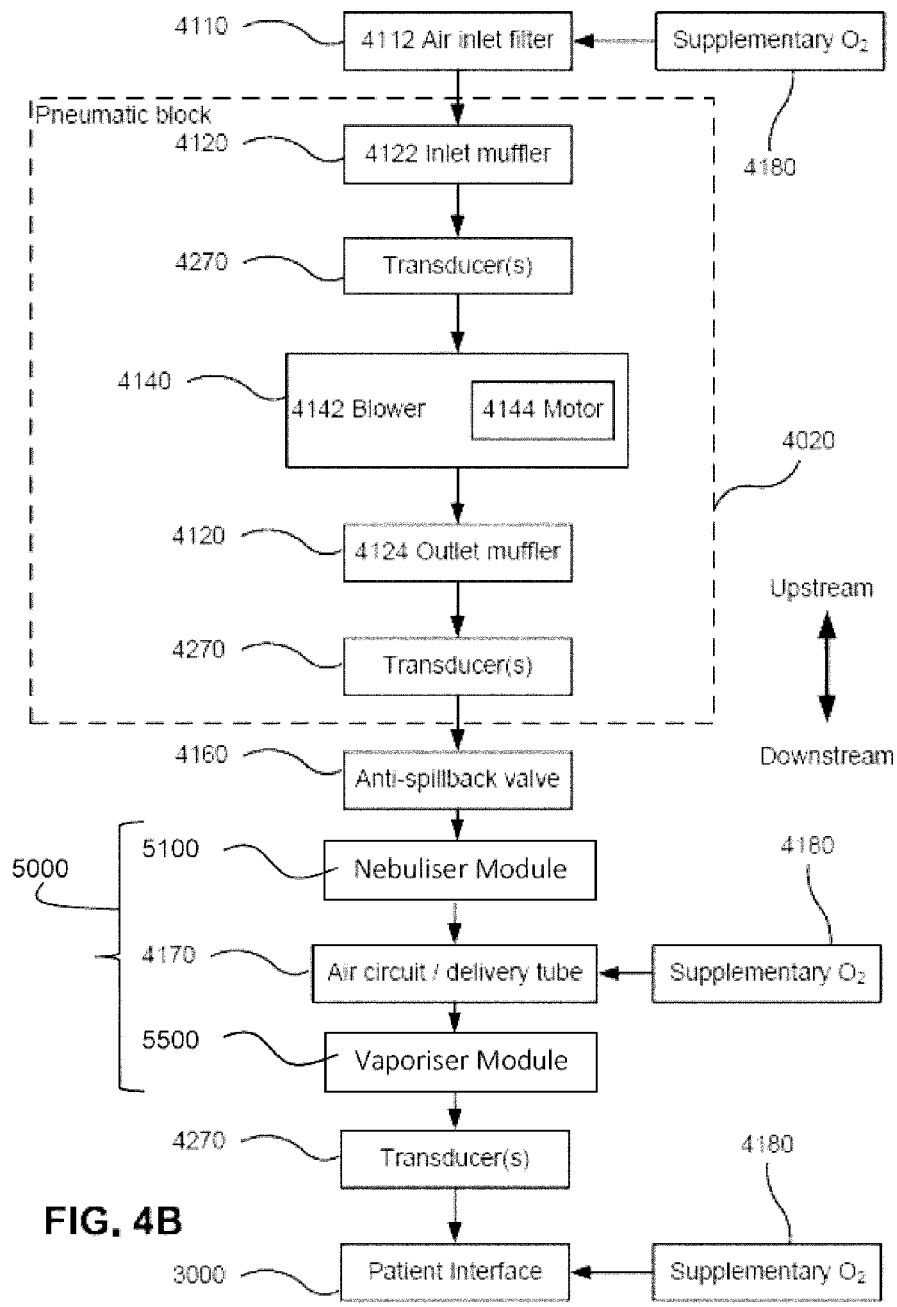
FIG. 4B is a schematic diagram of the pneumatic path of a RPT device in accordance with one form of the present technology. The directions of upstream and downstream are indicated.

The pneumatic path of the RPT device 4000, as seen in FIG. 4B, may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

Figure 4C:
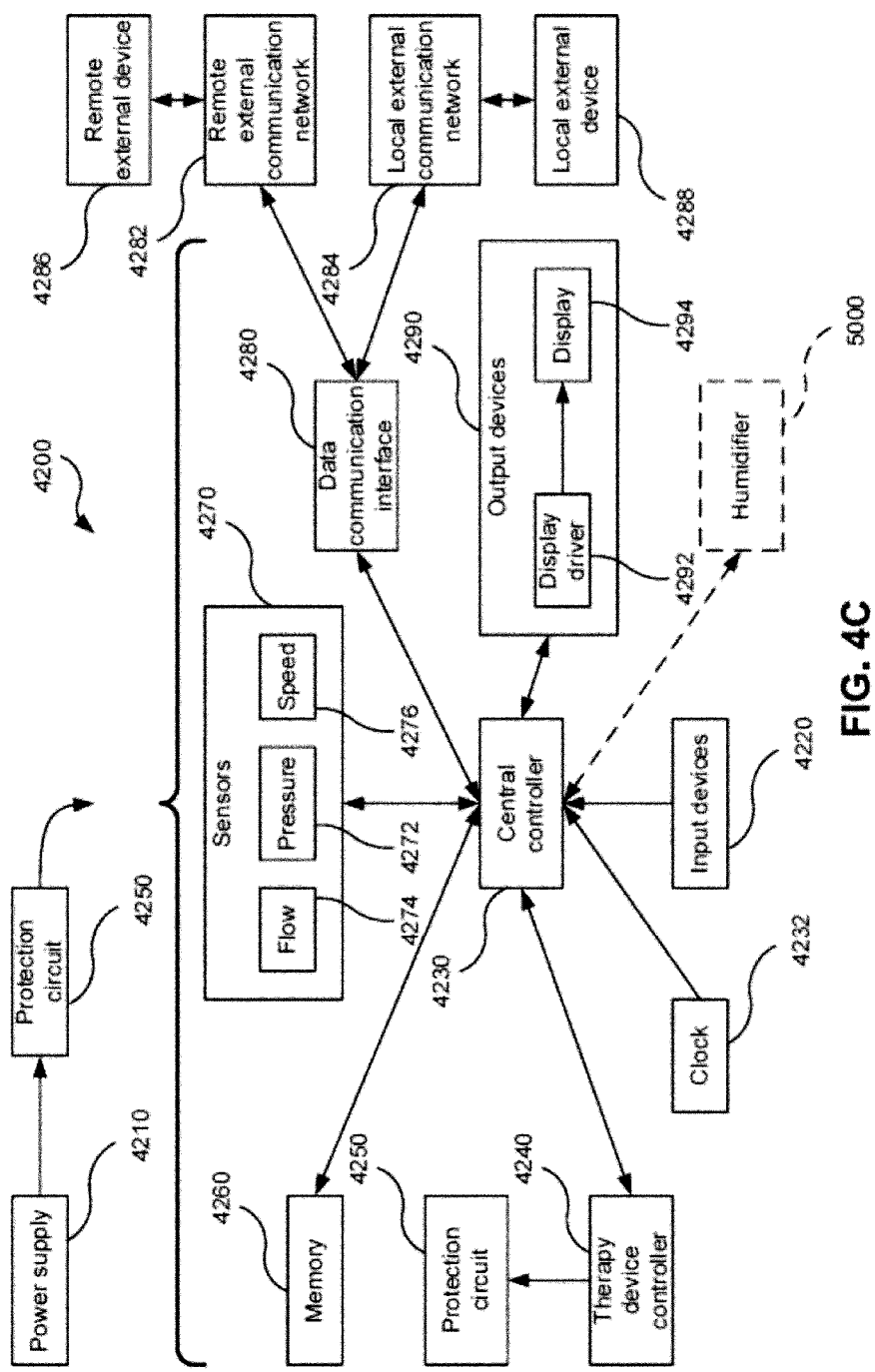
FIG. 4C is a schematic diagram of the electrical components of a RPT device in accordance with one form of the present technology.
Figure 4D:
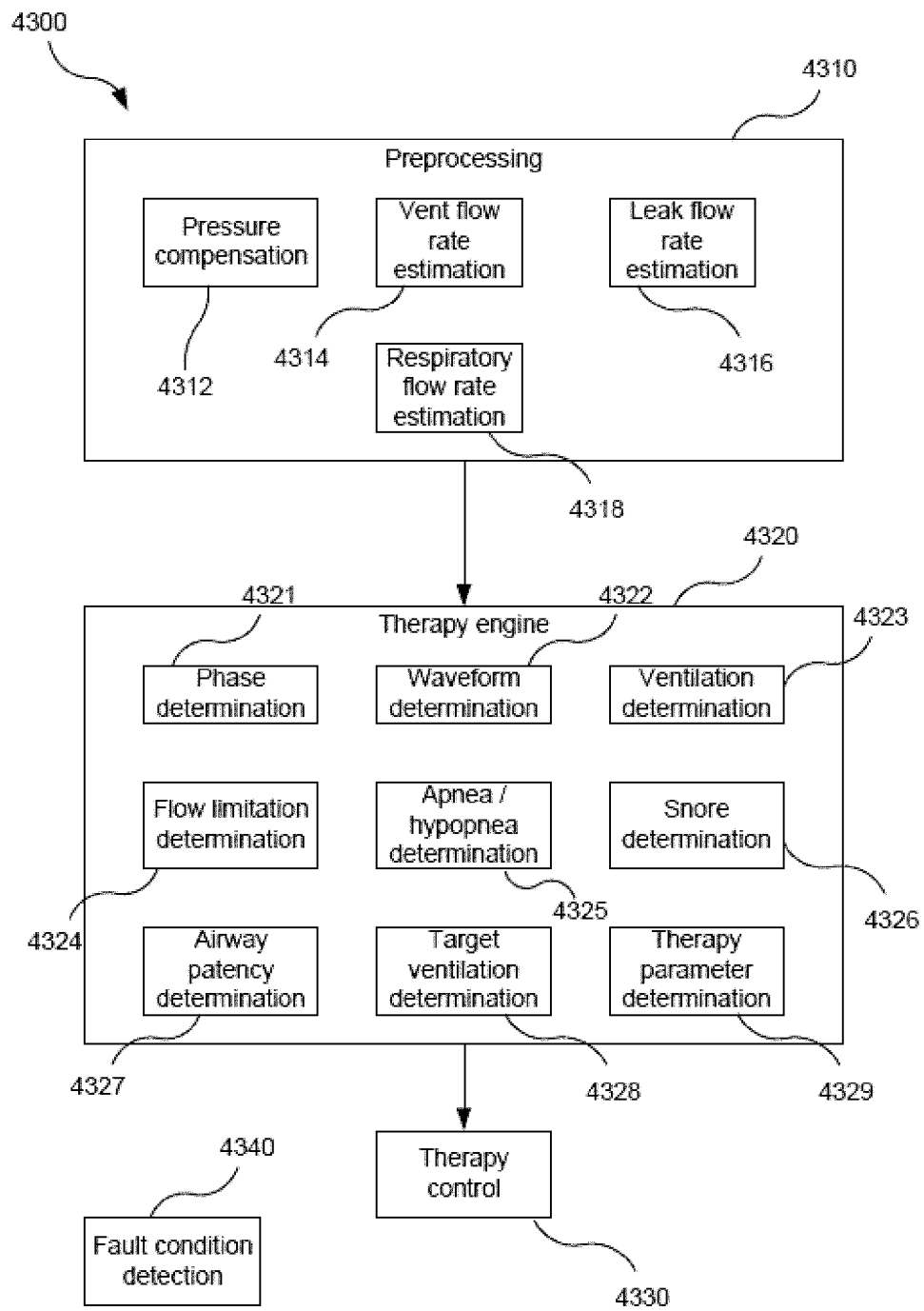
FIG. 4D is a schematic diagram of the algorithms implemented in a RPT device in accordance with one form of the present technology.
Figure 4E:
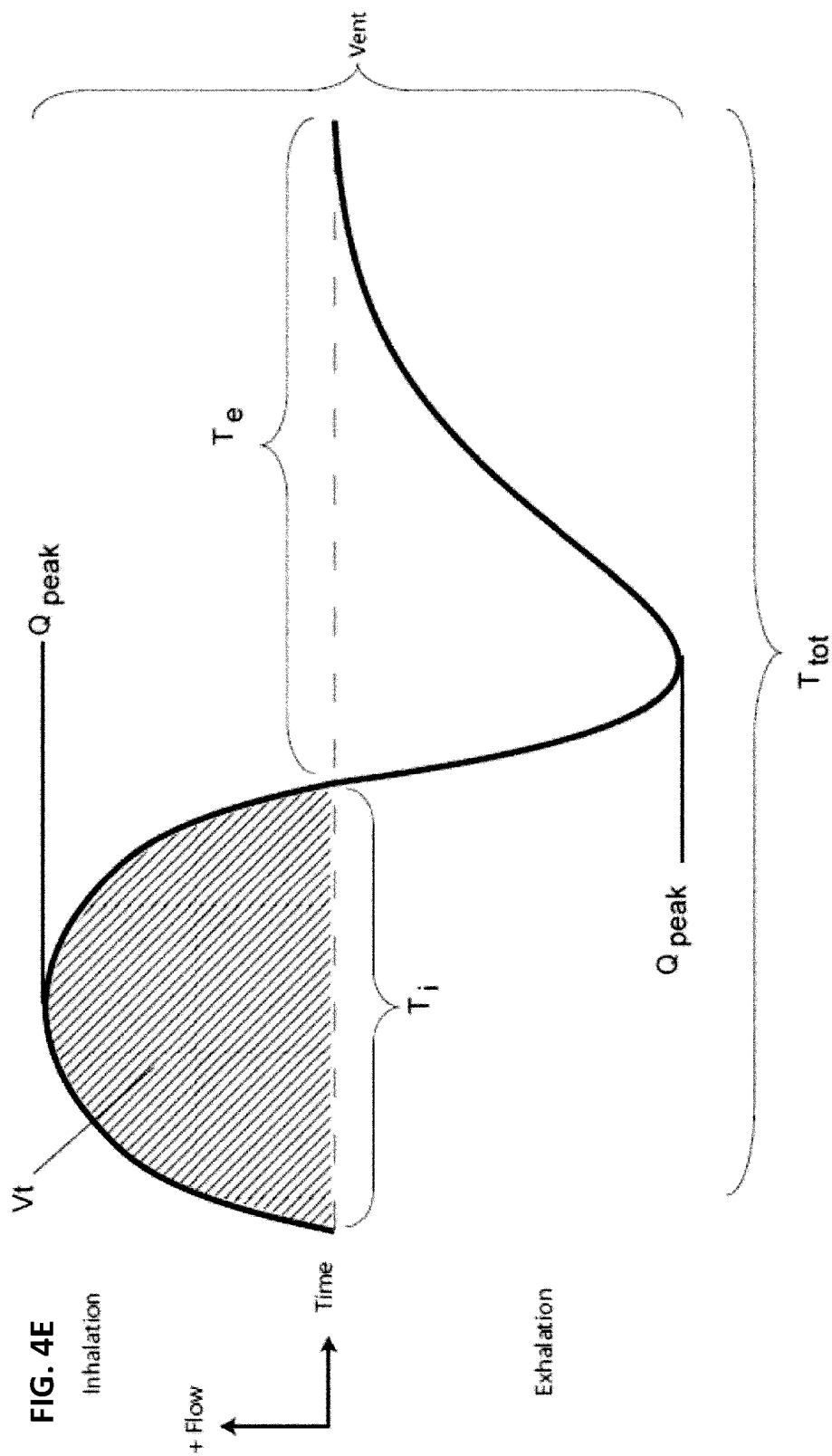
FIG. 4E shows a model typical breath waveform of a person while sleeping.
Figure 4F:
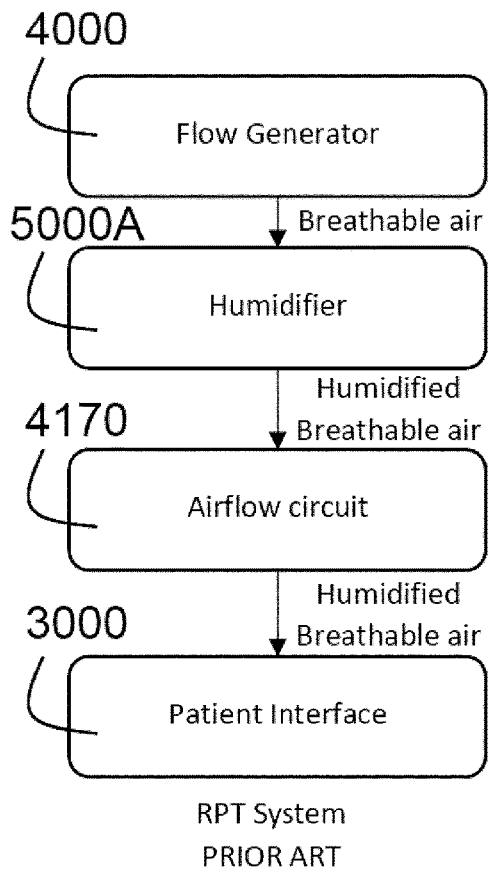
FIG. 4F shows the components of an example RPT system for treatment of a sleep disordered breathing condition in accordance with one form of the prior art.

An RPT device 4000 may comprise one or more of the following components in an integral unit, for example as seen in FIGS. 4B and 4C. In alternative forms, one or more of the following components may be located as respective separate units.

4.4.1.1 Pressure Generator

In one form of the present technology, a pressure generator 4140 for producing a flow, or a supply, of air at positive pressure is a controllable blower 4142. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

4.4.1.2 Transducer(s)

Transducers 4270 may be internal of the RPT device 4000, or external of the RPT device 4000. External transducers may be located for example on or form part of the air circuit 4170, e.g., the patient interface 3000. External transducers may be in the form of non-contact sensors such as a Doppler radar movement sensor that transmit or transfer data to the RPT device 4000.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

4.4.1.2.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

4.4.1.2.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

4.4.2 RPT Device Electrical Components

4.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier system 5000.

4.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

4.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In various forms of the present technology, the central controller 4230 may comprise one or more of a dedicated electronic circuit, an application-specific integrated circuit, and discrete electronic components.

The central controller 4230 may be configured to receive input signal(s) from one or more transducers 4270, one or more input devices 4220, and the humidifier system 5000.

The central controller 4230 may be configured to provide output signal(s) to one or more of an output device 4290, a therapy device controller 4240, a data communication interface 4280, and the humidifier system 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

4.4.2.4 Therapy Device Controller

In one form of the present technology, therapy device controller 4240 is a therapy control module 4330 that forms part of the algorithms 4300 executed by the central controller 4230.

4.4.2.5 Protection Circuits

The one or more protection circuits 4250 in accordance with the present technology may comprise an electrical protection circuit, a temperature and/or pressure safety circuit.

4.4.2.6 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

In one form of the present technology, the memory 4260 acts as a non-transitory computer readable storage medium on which is stored computer program instructions expressing the one or more methodologies described herein, such as the one or more algorithms 4300.

4.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260.

4.5 Humidifier System

4.5.1 Humidifier Overview

In one form of the present technology there is provided a humidifier system 5000. One purpose of a humidifier system 5000 is to change the absolute humidity and/or temperature of air or gas for delivery to a patient relative to ambient air. Typically, the humidifier system 5000 is used to increase the absolute humidity and increase the temperature of the flow of air (relative to ambient air) before delivery to the patient's airways.

FIGS. 1A-1C and 4F shows a schematic overview of the components of an example RPT system for treatment of a sleep disordered breathing condition comprising a RPT device 4000 for generating a flow of breathable air and a humidifier 5000a adapted to receive the flow of breathable air from the RPT device 4000 and output a flow of humidified breathable air to an air circuit 4170, whereupon the humidified air passes along the air circuit 4170 to a patient interface 3000 to be breathed by a patient 1000.

There are a plurality of available humidifier configurations.

Humidifier system 5000 may comprise a humidifier 5000a configured to change the absolute humidity of air or gas for delivery to a patient relative to ambient air. Additionally, or alternatively, a humidifier system 5000 may comprise one or more other components configured to change the temperature and/or the absolute humidity of air or gas for delivery to a patient relative to ambient air as described in relation to the following examples.

Figure 4G:
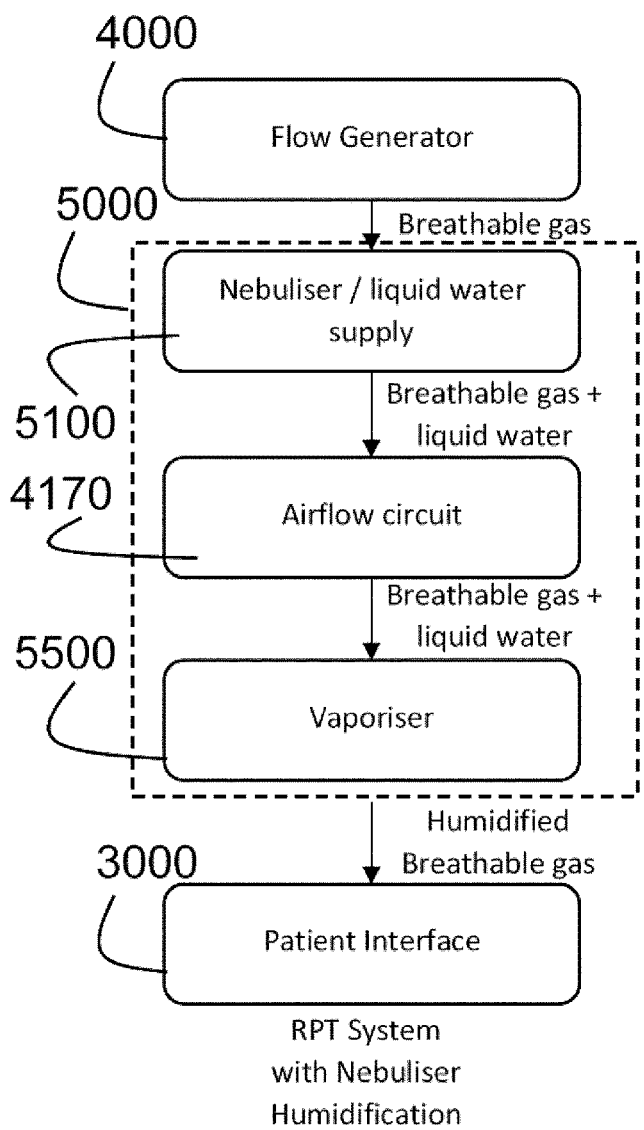
FIG. 4G is a schematic illustration of a RPT system incorporating a nebulising humidification system according to one form of the present technology.

FIG. 4G is a schematic illustration of a RPT system according to an example of the present technology and FIG.

5A shows an isometric view of the RPT system according to an example of the technology.

According to one aspect of the present technology, a humidifier system 5000 may comprise a nebuliser module 5100, configured to generate and deliver a nebula 5300 to an air circuit 4170 for delivery to a vaporiser module 5500 configured to evaporate the nebula 5300 to humidify a flow of air for delivery to a patient. The humidifier system 5000 may further comprise one or more of: a set of transducers, a heat-moisture exchanger, a vent and a controller.

As will be described, particular arrangements of humidification system 5000 in some forms of the technology may additionally comprise a filter 5600 adapted to be impermeable to liquid water ($H_2O$) but permeable to breathable gases generated by RPT device 4000 and also permeable to water vapour formed in vaporiser module 5500.

4.5.2 Humidifier Components

One or more components of a humidifier system may be modular; that is, removable from the rest of the humidifier system, for reasons such as, but not limited to, cleaning, repairs, replacement, or upgrade. However, in some forms, components (e.g. nebuliser module or vaporiser module) may not be removable from another component. In the present document, 'module' may be read as a 'subsystem' or 'component' rather than to be limited to arrangements of physical modularity.

4.5.2.1 Nebuliser Module

In one form, a nebuliser module 5100 comprises a water reservoir 5110, a nebuliser air inlet 5002 to receive a flow of air from a RPT device 4000, and a nebuliser outlet 5004 to deliver a flow of air comprising a fine mist (or nebula) of liquid (typically water).

4.5.2.1.1 Water Reservoir

According to one arrangement, the humidifier system 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier system 5000 may be configured to receive a supply of water from an external water source such as a building's water supply system.

According to one aspect as disclosed herein, the water reservoir 5110 is configured to store and/or provide liquid water to be added to a flow of air from the RPT device 4000 as the flow of air travels through the nebulising module 5100.

According to one form, the water reservoir 5110 may be removable from the remainder of the nebulising module 5100, for example, for filling of the reservoir. Alternatively, or additionally, the reservoir 5110 may comprise a lid 5112 which can be readily opened to facilitate filling of the reservoir 5110 with a suitable liquid such as, for example, water, through an opening without removing reservoir 5110 from the remainder of the nebuliser module 5100. In some forms of the technology the reservoir 5110 may have no lid or cover over the opening.

4.5.2.1.2 Nebuliser

The nebuliser module 5100 may comprise a nebuliser 5120 as shown schematically in FIG. 6.

The nebuliser module 5100 nebulises liquid from a water reservoir 5110 in order for the nebula 5300 to be admitted into the air path 5200 of the breathable air generated by RPT device 4000. The nebuliser may generate a nebula 5300 of liquid, the nebula 5300 comprising a particle size distribution suitable for transport by the flow of air for delivery to a vaporiser module. The nebuliser module 5100 may in some forms directly introduce the nebula 5300 into the air path. In some forms the nebuliser module may be configured to introduce the nebula 5300 in a parallel direction to the flow of air through the air path. In some forms, the nebuliser module may be configured to introduce the nebula 5300 in a perpendicular direction to the flow of air through the air path. It is recognised that in some forms the nebula is introduced to the flow of air in a way in which not all the liquid particles have the same direction of motion. In such cases the direction of introduction of the nebula may be understood to mean the direction of the average velocity vector of the liquid particles when they are introduced.

In some forms, the nebuliser 5120 may be configured to directly introduce nebula 5300 into the air path, for example the nebuliser 5120 may form part of the wall of the air path, for example by being located in an opening in the wall of the air path. In some forms, the nebula 5300 may be introduced into the air path via one or more additional components, for example the nebuliser 5120 may form part of the body of the water reservoir and connect to the air path via a nebuliser conduit or injection valve.

In particular arrangements, a nebuliser 5120 may include an aperture plate or a mesh positioned between the reservoir 5110 and the air path 5200, for example in an opening in a wall between the reservoir 5110 and the air path 5200, with one or more small holes (e.g., average of ~2 μm) that is connected to a vibrational element such as for example, a piezoelectric transducer or an ultrasonic horn driven by a piezoelectric element. Vibration of the vibrational element causes the mesh or aperture plate to vibrate, which causes liquid to move from the reservoir 5110 through the holes and into an air path 5200, converting the liquid to aerosolised particles (i.e., nebulising the liquid). In particular arrangements, the vibrational element may include a piezoelectric element. In particular arrangements, the piezoelectric element may comprise the aperture plate having the one or more holes. In some arrangements, the transducer may be indirectly connected to the mesh or aperture plate via one or more vibration transmission elements, for example in the form of a rod, which the vibrational element will vibrate and in turn causes the mesh or aperture plate to vibrate. In particular arrangements, nebuliser 5120 may include a pressure-based nebuliser that creates a pressure which forces liquid through one or more orifices so as to nebuliser the liquid in the reservoir 5110 and propel it into the air path 5200. It will be understood that any number of other known mechanisms to generate a nebula 5300 may be employed for a nebuliser 5120.

FIG. 7A shows a RPT device 4000 connected to a nebuliser module 5100 according to one form of the technology. Nebuliser housing 5130 may also comprise an inlet connection port 5135, adapted for pneumatic and/or electrical connection to RPT device 4000; outlet connection port 5140, adapted for both pneumatic and/or electrical connection to air circuit 4170; and air path 5200 between inlet connection port 5135 and outlet connection port 5140, wherein air path 5200 is in fluidic communication with reservoir 5110 via nebuliser 5120.

FIG. 7B shows an exploded view of reservoir 5110 comprising a lid 5112 and opening 5113 according to one form of the technology. In the arrangement, opening 5113 is adapted to receive nebuliser retaining collar 5115 and nebuliser 5120 such that nebuliser 5120 is integrated with reservoir 5110. In other arrangements, nebuliser 5120 may instead be integrated with nebuliser housing 5130. In this alternate arrangement, a replacement reservoir 5110 does not also need to incorporate the nebuliser 5120 hence beneficially making replacement reservoirs more cost effective.

FIG. 7C shows an exploded view of the nebuliser housing 5130 shown in FIG. 7A. The nebuliser housing 5130 comprises a frame 5131; a nebuliser activator unit 5121 comprising a vibrational element such as for example, a piezoelectric transducer; an inlet connection port 5135; an outlet connection port 5140; a nebuliser control circuitry 5150 comprising nebuliser controller 5240; and a housing cover 5137.

In the form of the technology illustrated in FIGS. 7A, 7B and 7C, reservoir 5110 is positioned above nebuliser housing 5130, through which air path 5200 passes. Nebuliser 5120 is positioned in or below an opening 5113 in the bottom of reservoir 5110 and liquid in reservoir 5110 is fed to the nebuliser 5120 under gravity. In other forms of the technology, the reservoir 5110 may be positioned horizontally adjacent to or below nebuliser housing 5130, through which air path 5200 passes. In one form, the walls of reservoir 5110 form part of the walls of nebuliser housing 5130.

FIGS. 7D and 7E show two alternate arrangements of a nebuliser module 5100 in other forms of the present technology, each including a reservoir 5110 for retaining liquid 5111, the reservoir being in fluid communication with air path 5200 via nebuliser 5120. In the forms of the technology shown in both figures the air path 5200 passes beneath the reservoir 5110 and the bottom wall of the reservoir 5110 is shared with or positioned adjacent to the upper wall defining the air path 5200.

In FIG. 7D air path 5200 passes linearly and horizontally through nebuliser housing 5130. Nebula 5300 injected into air path 5200 is picked up and carried along air circuit 4170 to vaporiser module 5500 (not shown) located at the distal end of air circuit 4170. In this arrangement, air flow must be fast enough such that nebula 5300 is entrained in the air flow so that the nebula 5300 may be delivered to the vaporiser module 5500 before it hits the bottom of air path 5200. If the nebula 5300 is not picked up, then nebula 5300 will accumulate as water in air path 5200 in addition to not reaching the vaporiser module 5500 for humidification. In FIG. 7E, air path 5200 includes a vertically oriented portion 5122 fluidly connected between two horizontally oriented portions 5123, the vertically oriented portion 5122 positioned directly beneath nebuliser 5120 such that nebula 5300 has a vertical distance to fall before impacting the bottom wall of air path 5200. Accordingly, the nebula 5300 has a greater chance of matching the velocity of the air flow from RPT device 4000 and thus being picked up and carried by the air flow along air circuit 4170 to vaporiser module 5500 located at the distal end of air circuit 4170. In other forms of the technology the air path 5200 may comprise a sloped portion positioned substantially below the nebuliser.

In another form the nebuliser 5120 comprises a floating element. The floating element floats in the liquid 5111 in the reservoir 5110. The floating element is configured such that at least part of its upper surface is exposed above the level of the liquid. In this arrangement, the nebuliser module is configured such that the air path 5200 passes across the top of the liquid 5111 in the reservoir 5110 and the top of the floating element is exposed to the air path 5200. The floating element may take any number of forms. In one example the floating element is torus-shaped.

FIGS. 7F and 7G are illustrations of a nebuliser module 5100 according to certain forms of the present technology. FIG. 7G shows a cross-sectional view along the dashed line in FIG. 7F. Nebuliser module 5100 comprises nebuliser housing 5130, a water reservoir 5110 with a lid 5112, as well as a nebuliser inlet 5002 for receiving a pressurised flow of air and a nebuliser outlet 5004 for delivering a flow of air containing a nebula 5300 of liquid water to another part of the RPT device 4000, for example air circuit 4170. Air path 5200 fluidly connects nebuliser inlet 5002 and nebuliser outlet 5004. The nebuliser module 5100 is arranged with the water reservoir 5110 positioned above air path 5200 so that there is a head of water to deliver water into nebuliser 5120 when the nebuliser valve 5125 is open.

Nebuliser module 5100 further comprises an electrical plug 5180, which may be in a bottom portion of a side wall of the nebuliser module 5100. In the embodiment shown the electrical plug 5180 is positioned in the same side wall as, and below, the nebuliser inlet 5002. Electrical plug may be configured to connect to the electrical components 4200 of the RPT device 4000. Nebuliser module 5100 also comprises an electrical socket 5170 for connecting the nebuliser control circuitry 5150 to the wire circuits 4171 of the air circuit 4170 which provide power and signalling to vaporiser module 5500. The electrical socket 5170 may be in a bottom portion of a side wall of the nebuliser module 5100. In the embodiment shown the electrical socket 5170 is positioned in the same side wall as, and below, the nebuliser outlet 5004. As shown in FIG. 7F, nebuliser module 5100 comprises an outlet connection port 5140 for connection to air circuit 4170.

FIG. 7G shows a nebuliser 5120 which is connected to water reservoir 5110 via a nebuliser valve 5125 and nebuliser valve seat 5126. Nebuliser valve 5125 is positioned in the bottom wall of the water reservoir 5110 and is adapted to control the flow of water from the reservoir to the nebuliser 5120. In the embodiment shown nebuliser 5120 is positioned below nebuliser valve 5125 and water admitted through the nebuliser valve 5125 is delivered to the nebuliser 5120 under gravity. Nebula inlet 5190 is positioned below nebuliser 5120 and delivers the nebula 5300 to the air path 5200. Nebula inlet 5190 may be provided in a wall of the air path 5200, for example the top wall as shown in FIG. 7G. The arrangement of the nebuliser 5120 and nebula inlet 5190 allows the nebula to be introduced into the air path 5200 in a direction (vertically downwards as shown in FIG. 7G) that is perpendicular to the direction of the flow of air through the air path (horizontally to the right as shown in FIG. 7G).

4.5.2.1.3 Water Level Indicator

The water reservoir 5110 may comprise a water level indicator 5160. In some forms, the water level indicator may provide one or more indications to a user such as the patient 1000 or a care giver regarding a quantity of the volume of water in the reservoir 5110. The one or more indications provided by the water level indicator may include an indication of a maximum, predetermined volume of water, any portions thereof, such as 25%, 50% or 75% or volumes such as 200 ml, 300 ml or 400 ml.

4.5.2.2 Humidifier Transducer(s)

The humidifier system 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5B. A humidifier transducer 5210 may produce one or more output signals which may be communicated to a controller such as the central controller 4230 and/or the humidifier controller 5250. In some forms, a humidifier transducer may be located externally to the humidifier system 5000 (such as in the air circuit 4170) while communicating the output signal to the controller.

4.5.2.2.1 Pressure Transducer

One or more air pressure transducers 5212 may be provided to the humidifier system 5000 in addition to, or instead of, a pressure sensor 4272 provided in the RPT device 4000.

4.5.2.2.2 Flow Rate Transducer

One or more air flow rate transducers 5214 may be provided to the humidifier system 5000 in addition to, or instead of, a flow rate sensor 4274 provided in the RPT device 4000.

4.5.2.2.3 Temperature Transducer

The humidifier system 5000 may comprise one or more temperature transducers 5216. The one or more temperature transducers 5216 may be configured to measure one or more temperatures such as of the heating element 5530 and/or of the flow of air downstream of the humidifier outlet 5004. In some forms, the humidifier system 5000 may further comprise a temperature sensor 5216 to detect the temperature of the ambient air.

4.5.2.2.4 Humidity Transducer

In one form, the humidifier system 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier system 5000.

The humidity sensor 5218 may be an absolute humidity sensor or a relative humidity sensor.

4.5.2.3 Nebuliser Controller

According to one arrangement of the present technology, humidifier system 5000 may comprise a nebuliser controller 5240, such as shown in FIG. 5B. In one form, the nebuliser controller 5240 forms part of humidifier controller 5250 and, in particular arrangements, may be a part of the central controller 4230. In another form, the nebuliser controller 5240 and the humidifier controller 5250 may each be a separate controller, which may be in communication with the central controller 4230. In some forms, the nebuliser module 5100 may comprise the nebuliser controller 5240 which may be electrically connected to humidifier controller 5250 and/or to the central controller 4230 of RPT device 4000 by electrical connections (not shown). Nebuliser housing 5130 in some forms may house a nebuliser controller 5240. In other forms the nebuliser controller 5240 may be located in the RPT device 4000.

In one form, the humidifier controller 5250 and/or the nebuliser controller 5240 may receive as inputs measures of properties (such as temperature, humidity, pressure and/or flow rate), for example of the flow of air, the water in the reservoir 5110. The nebuliser controller 5240 may also be configured to execute or implement humidifier algorithms and/or deliver one or more output signals. The nebuliser controller 5240 may be configured to reduce or increase the nebulisation rate based on the detection of the presence or absence of an optional heat and moisture exchange (HMX) module 5510. The nebuliser controller 5240 may also be configured to increase or decrease the nebulisation rate based on accumulation (nebulised water droplets that are trapped in the air circuit 4170), which can be estimated or detected by comparing the nebulisation rate against absolute humidity calculated from a Relative Humidity and Temperature (RHT) sensor. The RHT sensor may send a feedback signal 5230 to the vaporiser controller 5252 which may then send a heater control signal 5231 to the heating element 5530.

As shown in FIG. 5B, the humidifier controller 5250 may comprise one or more other controllers, such as a central humidifier controller 5251 and/or a vaporiser controller 5252 configured to control electronic components included in vaporiser module 5500 including, but not limited to, the temperature of a heating element 5530 and temperature, pressure, flow rate and/or humidity sensors located in vaporiser module 5500.

4.5.2.4 Air Circuit

In one form of the present technology an air circuit 4170 suitable for use in nebulising humidification system 5000 comprises a flexible conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface 3000. The air circuit 4170 may be referred to as an air delivery tube. In some cases, there may be separate limbs of the circuit for inhalation and exhalation. In other cases, a single limb is used.

In some forms, the air circuit 4170 may comprise one or more wire circuits configured to provide power and/or signalling between RPT device 4000 and electrical components included at the distal end of air circuit 4170 (i.e. proximal to patient interface 3000), for example control circuitry for vaporiser module 5500 and/or transducers provided in vaporiser module 5500 and/or patient interface 3000 such as, for example pressure, flow rate, temperature, and/or humidity sensors. The one or more wire circuits may comprise one or more transducers, such as temperature sensors. In one form, the wire circuit is located on the interior of the air circuit 4170, for example attached to the inner wall of the airflow conduit or floating independently within the conduit. In another form, the wire circuit is located on the exterior of the air circuit 4170, for example an external conduit could be aligned parallel to the axis of the fluid conduit or the wire circuit may be helically wound around the axis of the air circuit 4170. The airflow conduit may comprise more than one independent helical rib or conduit with, and/or another rib configured to include one or more electrical wires for data communications, and/or another rib configured to include electrical wires that may be used for heating of the airflow conduit, although this may not be necessary when using a nebuliser.

In particular arrangements, air circuit 4170 may comprise a hydrophobic coating on an inner surface of the conduit to minimise liquid accumulation on the inner wall of the air circuit 4170.

4.5.2.5 Vaporiser Module

A vaporiser module 5500 may be configured to receive the nebula 5300 from the nebuliser module 5100, and to evaporate the nebula 5300 to humidify the flow of air for delivery to the patient. The vaporiser module 5500 may be located proximal to the patient, such that the humidified air is not required to travel as far to reach the patient, thus reducing a risk of condensation en route to the patient. The patient interface 3000 may comprise at least a part of the vaporiser module 5500, such as in forms shown in FIGS. 8C and 8D, or the vaporiser module 5500 may be located on a separate component, such as together with the vent module 3410. In particular arrangements, vaporiser module 5500 comprises a vaporiser inlet 3250 configured for receiving a nebula 5300 in a flow of air from air circuit 4170 to which the vaporiser inlet 3250 is fluidly connected in use.

It will be understood that the vaporiser module is configured to cause a change in phase of liquid water in nebula 5300 to water vapour. In some forms of the technology the vaporiser module may achieve this phase change through boiling the liquid water in nebula 5300. In other forms, the liquid water in nebula 5300 may evaporate. Unless clearly indicated otherwise it will be understood that the term "vaporise" is intended to encompass both boiling and evaporation.

In particular arrangements, vaporiser module 5500 comprises one or more heating elements 5530. The heating element 5530 may be in communication with a controller such as a central humidifier controller 5251, nebuliser controller 5240, and/or vaporiser controller 5252. Vaporiser module 5500 optionally may comprise sensors 5210 including pressure, airflow, temperature and/or humidity sensors which can provide feedback input to humidifier controller 5250, nebuliser controller 5240 and/or vaporiser controller 5252 to enable control algorithms to control humidifier system 5000 to provide the desired temperature, humidity and positive pressure to the patient interface 3000.

Heating element 5530 and sensors 5210 may be controlled by vaporiser controller 5252 to provide sufficient heating to provide a humidified flow of air to the patient interface having the desired temperature, pressure and humidity characteristics for effective RPT treatment of patient 1000. A Printed Circuit Board (PCB) 5540 may be located in the vaporiser module 5500. PCB 5540 may comprise various electrical components which form part of vaporiser controller 5252.

In particular arrangements, the vaporiser module 5500 may also comprise an optional heat and moisture exchange (HMX) module 5510. One example of an HMX module 5510 is described in United States Patent Application Publication No. 2016/0175552, which is incorporated herein in by reference its entirety. The HMX module 5510 may be positioned downstream (i.e. patient side) of the vaporiser module 5500 in the RPT system.

In some configurations, the vaporiser module 5500 may be configured to receive a supply of water for humidifying the flow of air in addition to the supply of water from the nebuliser. For example, the vaporiser module may be configured to receive liquid water pumped through a flow conduit to the heating element. The flow conduit may be located either within the air circuit 4170 or external to the air circuit 4170.

FIGS. 8A and 8B are illustrations of a vaporiser module 5500 according to certain forms of the present technology. FIGS. 8C and 8D are illustrations of a vaporiser module 5500 provided to a patient interface 3000 according to different forms of the present technology. FIGS. 8E and 8F are cross-sectional views of vaporiser module 5500 attached to part of an air circuit 4170 according to different forms of the present technology.

In some forms of the technology, the patient interface 3000 may be directly connectable to the vaporiser module 5500. The patient interface 3000 may comprise a supporting structure to hold a vaporiser module 5500 in position, wherein the supporting structure may comprise one or more surfaces surrounding an opening in the plenum chamber 3200. In the forms of patient interface 3000 shown in FIGS. 8C and 8D the opening in the plenum chamber 3200 is on an anterior side of the patient interface during use. The opening is shaped and structured to substantially match a vaporiser outlet 3260 in a posterior side of the vaporiser module 5500. One or more connecting surfaces 3451 surround the vaporiser outlet 3260 and are structured to sealingly mate with complementary connecting surfaces on the plenum chamber 3200 surrounding the opening therein.

The vaporiser module 5500 may be configured to be removably coupled to the patient interface 3000, such as with the plenum chamber 3200. The vaporiser module 5500 may comprise a tab 3450 configured to be received by the patient interface, or to be connectable to the patient interface via a snap fit. The connecting surfaces of the plenum chamber 3200 and/or the vaporiser module 5500 may comprise one or more flanges and/or seals to facilitate a substantially sealed connection therebetween.

It will be appreciated that the connection port or inlet of the patient interface 3000 may be indirectly connected to air circuit 4170 through the vaporiser module 5500, as is the case in the forms of the technology shown in FIGS. 8D and 8E.

Vaporiser module 5500 may comprise a vaporiser housing 3410 as shown in FIGS. 8A and 8B. The vaporiser housing 3410 may comprise a vent 3400, for example positioned on its anterior side during use, and a vaporiser outlet 3260, for example positioned on its posterior side during use. The vaporiser housing 3410 may be adapted to removably engage to a plenum chamber 3200 of patient interface 3000. The vaporiser housing 3410 may locate the vaporiser module 5500 in a flow path of breathable gas within a plenum chamber 3200 of the patient interface 3000 and may orient the heating element 5530 of the vaporiser module 5500 to be substantially in line with or parallel to a flow path of the flow of breathable gas, thereby allowing flow through the vaporiser module 5500. The positioning of the vaporiser module 5500 in close proximity to the entrance of the patient's airways may maximise the efficiency of the humidification of the breathable air from RPT device 4000 and minimise the opportunity for humidified air exiting the vaporiser module 5500 from condensing to liquid water prior to being inhaled by the patient 1000.

A vaporiser housing 3410 comprising vaporiser module 5500 shown in FIG. 8B, and shown in engagement respectively with a pillows-type patient interface 3001 and a full-face-type patient interface 3003 in FIGS. 8D and 8E, may fluidly connect an interior chamber of the vaporiser module 5500 with the plenum chamber 3200 of the patient interface 3000 and may divide said plenum chamber 3200 into an anterior side of the plenum chamber and a posterior side of the plenum chamber. This positioning of the vaporiser module 5500 may position the vent 3400 on an anterior (upstream, i.e. humidifier) side of the heating element 5530 during use with the entrance of the patient's airways on a posterior (downstream, i.e. patient) side of the vaporiser module 5500. This configuration may allow the flow of exhaled gas from the patient to flow into the posterior side of the plenum chamber prior to venting, which allows any water vapour in the exhaled air to be retained in the heating element 5530 prior to being lost out of the vent 3400. This recaptured water vapour may then be re-vaporised by heating element 5530 and may enter the air flow of the patient's next inhalation, thus assisting the efficiency of the humidifier 5000 by not requiring as much water in the form of nebula 5300 delivered from nebuliser module 5100 in order to produce breathable air of sufficient humidity for the comfort of patient 1000.

It is also possible to position an auxiliary vent on the posterior side of the vaporiser module 5500 in the plenum chamber 3200 to offset $CO_2$ build up within this volume. For example, in the case of a full face mask, the additional volume in the plenum chamber 3200 (i.e., dead space volume) in comparison to smaller masks, may lead to unwanted and/or excessive $CO_2$ build up occurring within this space. To mitigate this effect, an auxiliary vent may be positioned proximal to the patient's airways, on the posterior or patient side of the vaporiser module 5500. Positioning an auxiliary vent on the posterior side of the vaporiser module 5500 will result in some venting of the humidified flow of breathable gases prior to delivery to the patient. To compensate for this venting of humidified air, the overall humidification performance may be maintained by increasing the ability of the vaporiser module 5500 and/or nebuliser module 5100 to humidify the flow of breathable gas within a predetermined volume of the plenum chamber 3200.

The vaporiser housing 3410 may also include a baffle to separate the incoming flow of breathable gas from the flow of $CO_2$ washout. The baffle may separate these flows of gas from one another such that these flows of gas do not interfere with one another. U.S. Pat. No. 7,934,501, which is incorporated herein by reference in its entirety, describes further examples and features of baffles that may be applicable to the exemplary patient interface 3000.

FIGS. 8E and 8F show schematic cross-sectional views of vaporiser module 5500 along line A-A of FIG. 8B. A vaporiser inlet 3250 of vaporiser module 5500 is pneumatically connected to the distal end of air circuit 4170 by a connection collar 4172. Air circuit 4170 comprises wire circuits 4171 to provide power and signalling to vaporiser module 5500. Wire circuits 4171 are contained within helically wound ribs 4173 on outer surface of air conduit 4170. In use, aerosol droplets of liquid water in nebula 5300 are transported by airflow 5400 along air circuit 4170 to vaporiser module 5500. Liquid water droplets on reaching vaporiser module 5500 are vaporised by the heating element 5530. In some forms, the heating element 5530 is formed from a thermally conductive material. In some forms, the heating element 5530 presents a labyrinthine path for nebula 5300 and airflow 5400 to improve the adsorption of liquid water droplets of nebula 5300 onto a surface of the heating element 5530, and to improve vaporisation of the adsorbed nebula 5300 into the air path. In some forms, the heating element 5530 comprises one or more of: a metal, a polymer, or a ceramic. Suitable examples of heating element 5530 may include a metal foam, or a porous polymer.

FIGS. 9A and 9B are illustrations of a vaporiser module 5500 according to certain forms of the present technology. In particular arrangements, the vaporiser module 5500 may be in the form of an in-line module, i.e. positioned in the air circuit in the path of the air flow, distal from the patient interface 3000. Vaporiser module 5500 comprises a vaporiser inlet 3250 configured to fluidly connect to an upstream portion of an air circuit 4170 for receiving a nebula 5300 in a flow of air from a nebuliser module 5100. Vaporiser module 5500 further comprises a vaporiser outlet 3260 configured to fluidly connect to a downstream portion of an air circuit 4170 for delivering a humidified flow of air to a patient interface 3000. Vaporiser module 5500 may also comprise humidifier sensors 5210 and a protective cover 5220 for the humidifier sensors 5210. The humidifier sensors 5210 may provide feedback signals to the humidifier controller 5250. The humidifier sensors 5210, as shown in FIG. 9B, may be located on a rectangular protrusion and positioned in the air flow path. PCB 5540 may be located in the vaporiser module 5500, as shown in FIG. 9B. PCB 5540 may be configured to have a shape in order that it is able to fit compactly in the vaporiser module 5500. For example, as shown in FIG. 9B, PCB 5540 is shaped to fit around the outer circumference of the air flow path through vaporiser module 5500.

Vaporiser module 5500 may also comprise a heating element 5530 and a housing 5535 for the heating element 5530. In some forms, the heating element 5530 is in the form of a pin array 5531, as shown in FIG. 9B. The heating element 5530 comprising a central plate 5532 from which pin-shaped projections extend on one or (in the case of the embodiment of FIG. 9B) both sides of the central plate 5532. In the form of the technology shown in FIG. 9B the pins extend parallel to a longitudinal axis of the vaporiser module 5500 and parallel to the direction of air flow through the vaporiser module 5500. In other forms of the technology the pins of pin array 5531 extend in another direction, for example perpendicular to the direction of air flow. The central plate 5532 may comprise a film heater to heat the pin array 5531. In the embodiment shown in FIG. 9B the central plate 5532 is arranged inside vaporiser module 5500 so that there is a space or spaces between its outer circumference and the inner walls of housing 5535 for the flow of air to pass around it. The pin array 5531 provides a large surface area for contact between the heating element 5530 and the nebula in the flow of air.

In some forms, the heating element 5530 has a structure to provide a tortuous air path. For example, the heating element may be helicoid. The axis of the helicoid may be parallel to the direction of the flow of air through the vaporiser module 5500. The helicoid structure may comprise a rod heater at its centre to heat the heating element 5530.

In some forms, the heating element 5530 is formed of a high electrical impedance material, in which case it may be connected to an electrical circuit and be heated by resistive heating to vaporise the adsorbed nebula 5300. One suitable example may be a resistive, porous ceramic element. In alternative forms, the heating element 5530 is formed of a low electrical impedance material and a second heating component may be needed. A second heating component may be provided in the vaporiser module 5500 and thermally coupled to the heating element 5530 to provide heat for vaporisation of the nebula 5300. In one form, the second heating component is provided in direct contact with the heating element 5530 such that in operation the second heating component heats heating element 5530 to facilitate vaporisation of liquid water droplets adsorbed onto a surface of the heating element 5530. Airflow 5400 as it passes through heating element 5530 takes up the vaporised water droplets to form a humidified airflow 5410 exiting vaporiser module 5500 to be delivered at a controllable temperature and humidity to patient interface 3000 for inhalation by patient 1000. Heating element 5530 may beneficially provide heat to airflow 5400 as it passes therethrough for delivery to the patient at a comfortable temperature.

A potential disadvantage of transporting liquid water to a point proximal to patient interface 3000 is that liquid water can transport bacteria which may undesirably be inhaled by patient 1000. In comparison, bacteria cannot be transported by water vapour in a humidified flow of air. Accordingly, particular care must be taken with the operation of vaporiser module 5500 to ensure that all liquid water droplets of nebula 5300 is adsorbed by a heating element 5530 and vaporised into water vapour to prevent the possible transfer of bacteria to patient 1000. Optionally, a liquid filter 5600 may be provided downstream of the heating element 5530. Filter 5600 is adapted such that water vapour is permitted to pass through filter 5600, but residual liquid water which may pass through heating element 5530 is blocked by filter 5600, thus reducing any potentially bacteria-laden liquid water droplets reaching the patient 1000. In further arrangements, where an optional HMX 5510 may be provided in vaporiser module 5500, the HMX 5510 would also act as a liquid filter only allowing humidified air containing water vapour to pass therethrough.

4.5.3 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

4.6 Certain Advantages of the Technology

An advantage of certain forms of the present technology is reducing or eliminating a need to heat the air circuit or a humidifier tub.

In prior devices, which require the heating of a large volume of water to humidify the air supply, it can take a long time for the level of humidity to be acceptable for patient breathing. An advantage of certain forms of the present technology is a more rapid change in the level of humidity, compared to prior art devices.

An advantage of certain forms of the present technology compared to prior devices which require heating liquid in a humidifier tub, is that there is a reduced risk of overheating of a reservoir, and potentially damaging a bedside table, the humidifier and/or the RPT device. For example, as can be caused if the liquid in the reservoir is exhausted but a heating element keeps emitting heat. In the presently described technology, should the reservoir run dry the only consequence is the patient receives dry air.

An advantage of the certain forms of the present technology compared to prior devices is that the addition of a nebula to the airflow provides cooling of the airflow via evaporative cooling mechanisms. It is therefore possible to provide air to the patient which is below ambient air temperature, which may be beneficial under particular circumstances, such as in hot climates.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

4.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.7.2 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilised to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilised, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A treatment system for treating a respiratory disorder in a patient, the system comprising:
    a respiratory pressure therapy device with a blower configured to generate a flow of air at a positive pressure with respect to ambient pressure;
    an air circuit configured to transport the flow of air to a patient interface, the air circuit having a first end connected to the respiratory pressure therapy device and a second end opposite the first end;
    a water reservoir configured to retain a volume of water for humidification of the flow of air;
    a nebuliser configured to receive water from the water reservoir and to generate a nebula, and to admit the nebula into the flow of air for delivery to a vaporiser module via the air circuit; and the vaporiser module comprising a heating element, the vaporiser module being configured to receive the nebula from the second end of the air circuit, and the heating element being configured to generate heat to vaporise the received nebula to humidify the flow of air.

2. The system of claim 1, wherein the vaporiser module is directly connectable to the patient interface.

3. The system of claim 1, wherein the heating element is formed of a thermally conductive material comprising one or more of a metal, a polymer, or a ceramic.

4. The system of claim 1, wherein the vaporiser module comprises a labyrinthine path therethrough for the nebula and the flow of air.

5. The system of claim 1, wherein the nebuliser is configured to admit the nebula into the flow of air parallel to the flow of air.

6. The system of claim 1, further comprising a nebulizer module that includes the nebuliser and the water reservoir.

7. The system of claim 6, wherein the nebuliser is configured to float in the water reservoir.

8. The system of claim 1, wherein the nebuliser is located proximal to the respiratory pressure therapy device.

9. The system of claim 1, wherein the air circuit is located between the nebuliser and the vaporiser module.

10. The system of claim 1, further comprising a liquid filter located downstream of the vaporiser module and configured to block passage of liquid water therethrough.

11. The system of claim 1, wherein the air circuit comprises a wire circuit to provide power and signalling to the vaporiser module.

12. The system of claim 1, wherein the air circuit further comprises a hydrophobic coating on an inner surface thereof.

13. The system of claim 1, wherein the vaporiser module comprises a heat and moisture exchange (HMX) module.

14. The system of claim 13, wherein the HMX module is located downstream of the heating element.

15. The system of claim 14, wherein the HMX module acts as a filter and blocks passage of liquid water therethrough.

16. A nebuliser apparatus for a respiratory treatment system, the respiratory treatment system for treating a respiratory disorder in a patient, the nebuliser apparatus comprising:
an air inlet for receiving a flow of air at a positive pressure with respect to ambient pressure;
a nebuliser configured to:
receive a supply of water;
generate a nebula from the supply of water; and
admit the nebula into the flow of air; and
an outlet for the flow of air comprising the nebula,
wherein the nebuliser is configured to admit the nebula into the flow of air by downwardly dispensing the nebula into the flow of air parallel to and in a same direction as the flow of air.

17. The nebuliser apparatus of claim 16, wherein the nebuliser apparatus comprises a water reservoir configured to retain a volume of water, the nebuliser being configured to receive the supply of water from the water reservoir.

18. The nebuliser apparatus of claim 17, wherein the nebuliser is configured to float in the water reservoir.

* * * * *